United States Patent
Baroni et al.

(10) Patent No.: US 8,193,190 B2
(45) Date of Patent: Jun. 5, 2012

(54) DERIVATIVES OF (BRIDGED PIPERAZINYL)-1-ALKANONE AND USE THEREOF AS P75 INHIBITORS

(75) Inventors: Marco Baroni, Paris (FR); Françoise Bono, Paris (FR); Sandrine Delbary-Gossart, Paris (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/966,413

(22) Filed: Dec. 13, 2010

(65) Prior Publication Data

US 2011/0144116 A1 Jun. 16, 2011

Related U.S. Application Data

(63) Continuation of application No. PCT/FR2009/051118, filed on Jun. 12, 2009.

(30) Foreign Application Priority Data

Jun. 13, 2008 (FR) ...................................... 08 03299

(51) Int. Cl.
*A61K 31/4995* (2006.01)
(52) U.S. Cl. .......................... 514/249; 544/295; 544/349
(58) Field of Classification Search .................. 544/295, 544/349
See application file for complete search history.

(56) References Cited

U.S. PATENT DOCUMENTS

| 7,423,039 B2 | 9/2008 | Dos Santos et al. |
| 7,468,368 B2 | 12/2008 | Bono et al. |
| 7,652,011 B2 | 1/2010 | Bosch et al. |

FOREIGN PATENT DOCUMENTS

| WO | WO 00/59893 | 10/2000 |
| WO | WO 03/104225 | 12/2003 |
| WO | WO 2005/054227 | 6/2005 |
| WO | WO 2005/054229 | 6/2005 |

OTHER PUBLICATIONS

Weskamp, G., et al., Evidence That Biological Activity of NGF is Mediated Through a Novel Subclass of High Affinity Receptors, Neuron, vol. 6, pp. 649-663, (1991).
Della-Bianca, V., et al., Neurotrophin P75 Receptor is involved in Neuronal Damage by Prion Peptide-(106-126), The Journal of Biological Chemistry, vol. 276, No. 42, (2001), pp. 38929-38933.
Friedman, W. J., et al., Neurotrophin Signaling Via Trks and P75, Experimental Cell Research, vol. 253, pp. 131-142, (1999).
Longo, F. M., et al., Small Molecule Neurotrophin Receptor Ligands: Novel Strategies for Targeting Alzheimer's Disease Mechanisms, Current Alzheimer Research, (2007), vol. 4, pp. 503-506.
Lowry, K., et al., A Potential Role for the P75 Low-Affinity Neurotrophin Receptor in Spinal Motor Neuron Degeneration in Murine and Human Amyotrophic Lateral Sclerosis, Amyotroph. Lateral. Scler. (2001), vol. 2, pp. 127-134.
Perlman H., et al., Evidence for the Rapid Onset of Apoptosis in Medial Smooth Muscle Cells After Balloon Injury, Circulation, (1997), vol. 95, pp. 981-987.
Rabizadeh, S., et al., Expression of the Low-Affinity Nerve Growth Factor Receptor Enhances B-Amyloid Peptide Toxicity, Proc. Natl. Acad. Sci. USA, vol. 91, pp. 10703-10706, (1994).
Raychaudhuri, S. P., et al., Role of NGF and Neurogenic Inflammation in the Pathogenesis of Psoriasis, Progress in Brain Research, vol. 146, pp. 433-437, (2004).
Rihl, M., et al., Involvement of Neurotrophins and Their Receptors in Spondyloarthritis Synovitis: Relation to Inflammation and Response to Treatment, Ann Rheum Dis, (2005), vol. 64, pp. 1542-1549.
Roux. P. P., et al., P75 Neurotrohpin Receptor Expression is Induced in Apoptotic Neurons After Seizure, The Journal of Neuroscience, (1999), vol. 19, No. 16, pp. 6887-6896.
Sanguinetti, M. C., et al., HERG Potassium Channels and Cardiac Arrhythmia, Nature, vol. 440, pp. 463-464 (2006).
Tokuoka, S., et al. Disruption of Antigen-Induced Airway Inflammation and Airway Hyper-Responsiveness in Low Affinity Neurotrophin Receptor P75 Gene Deficient Mice, British Journal of Pharmacology, (2001), vol. 134, pp. 1580-1586.
Chaldakov, G. N., et al., Neurotrophin Presence in Humans Coronary Atherosclerosis and Metabolic Syndrome: a Role for NGF and BDNF in Cardiovascular Disease, Progress in Brain Research, vol. 146, pp. 279-289, (2004).

*Primary Examiner* — James O. Wilson
*Assistant Examiner* — Brian McDowell
(74) *Attorney, Agent, or Firm* — Ronald G. Ort

(57) ABSTRACT

The present invention relates to derivatives of ((phenyl)-3,6-dihydropyridin-1-yl)(bridged piperazinyl)-1-alkanone derivatives and ((phenyl)-2,5-dihydropyrrol-1-yl) (bridged piperazinyl)-1-alkanone corresponding to Formula (I):

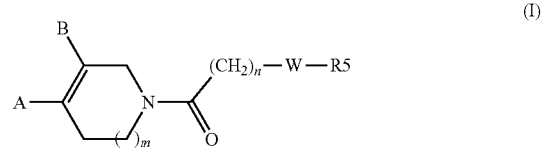

(I)

in which the variables are as defined herein, to the preparation thereof and to the therapeutic use thereof.

12 Claims, No Drawings

DERIVATIVES OF (BRIDGED PIPERAZINYL)-1-ALKANONE AND USE THEREOF AS P75 INHIBITORS

The present invention relates to ((phenyl)-3,6-dihydropyridin-1-yl)(bridged piperazinyl)-1-alkanone derivatives and ((phenyl)-2,5-dihydropyrrol-1-yl) (bridged piperazinyl)-1-alkanone derivatives, to the preparation thereof and to the therapeutic use thereof.

The compounds according to the present invention have an affinity for the p75$^{NTR}$ neurotrophin receptor.

Neurotrophins belong to a family of proteins of which the biological effect is in particular cell survival and differentiation.

The p75$^{NTR}$ receptor, which is a receptor for all neurotrophins, is a transmembrane glycoprotein of the tumour necrosis factor (TNF) receptor family (W. J. Friedman and L. A. Greene, Exp. Cell. Res., 1999, 253, 131-142). The p75$^{NTR}$ receptor is expressed in several cell types, and several biological functions are assigned thereto: firstly, modulation of the affinity of neurotrophins for receptor tyrosine kinases (trk); secondly, in the absence of trk, induction of a signal for cell death by apoptosis. Moreover, the neurotrophin precursors, proneurotrophins, are capable of binding to p75$^{NTR}$ with high affinity, and are considered to be powerful inducers of p75$^{NTR}$-dependent apoptosis in neurons and certain cell lines.

In the central nervous system, many studies show that apoptosis is involved in several pathologies, such as amyotrophic lateral sclerosis, multiple sclerosis, Alzheimer's disease, Parkinson's disease, Huntington's disease and prion diseases. p75$^{NTR}$ is also known to be overexpressed in various types of neurodegenerative diseases, such as Alzheimer's disease and amyotrophic lateral sclerosis (ALS) (Longo F. M. et al., Curr. Alzheimer Res. 2007; 4: 503-506; Lowry K. S. et al., Amyotroph. Lateral. Scler. Other. Motor. Neuron. Disord. 2001; 2: 127-34).

Results suggest that p75$^{NTR}$ may play a predominant role in the mechanisms resulting in post-ischaemia apoptotic neuronal death (P. P. Roux et al., J. Neurosci., 1999, 19, 6887-6896).

Results (V. Della-Bianca et al., J. Biol. Chem., 2001, 276: 38929-33), (S. Rabizadeh et al., Proc. Natl. Acad. Sci. USA, 1994, 91, 10703-10706) support the hypothesis that p75$^{NTR}$ plays an important role in neuronal death induced by the infectious prion protein (transmissible spongiform encephalopathy) or by the beta-amyloid protein (Alzheimer's disease).

The p75$^{NTR}$ receptor is also associated with the Nogo receptor and involved in the signalling of the inhibitory effects of this myelin protein with respect to axon growth. As a result, the p75$^{NTR}$ receptor plays a major role in the regulation of neuronal plasticity and in neuron-glia interactions, and thus represents a therapeutic target of choice for promoting nerve regeneration.

Outside the nervous system and neurodegenerative diseases, it has been suggested that p75$^{NTR}$ could play a role in cardiovascular diseases such as atherosclerosis and myocardial ischaemia (M. L. Bochaton-Pialat et al., Am. J. Pathol., 1995, 146, 1-6; H. Perlman, Circulation, 1997, 95, 981-987). Recent studies show an increase in the expression of p75$^{NTR}$ and of neurotrophins, and massive apoptosis, in atherosclerotic lesions.

Several studies also suggest that p75$^{NTR}$ is an inflammation mediator (Rihl M. et al., Ann. Rheum. Dis. 2005: 64(11): 1542-9; Raychaudhuri S. P. et al., Prog. Brain. Res. 2004; 146: 433-7, Tokuoka S. et al., Br. J. Pharmacol. 2001, 134: 1580-1586).

p75$^{NTR}$ also plays an essential role in tumour biology.

Many compounds are known to interact with the trkA/NGF/p75$^{NTR}$ system or to have an NGF (nerve growth factor) type activity. Thus, patent application WO 00/59893 describes substituted pyrimidine derivatives which exhibit NGF-type activity and/or which increase the activity of NGF on PC12 cells.

Patent application WO 03/104225 describes compounds which exhibit affinity for p75$^{NTR}$ receptors. These compounds are highly metabolised and exhibit high percentages of inhibition of the hERG gene (human Ether a go-go Related Gene).

The hERG gene encodes the K$_v$11.1. protein of a potassium ion channel. This protein is known through its contribution to the electrical activity of the heart. When the ability of the channel to conduct the electric current through the cell membrane is inhibited by the action of medicaments, it can result in a potentially fatal condition known as QT syndrome. A certain number of medicaments have inhibited this protein, creating a concomitant risk of sudden death as an adverse side effect. This has made hERG inhibition a central question both in the regulation of medicaments and in the development thereof (Sanguinetti M C, Tristani-Firouzi M (March 2006). "hERG potassium channels and cardiac arrhythmia". *Nature* 440 (7083): 463-9).

The subject of the present invention is novel compounds which have an affinity for p75$^{NTR}$ receptors and which do not have the drawbacks of high metabolisation and strong hERG inhibition that the prior art compounds have. It therefore displays an advantage for the development of new medicaments.

The subject of the present invention is the compounds corresponding to Formula (I):

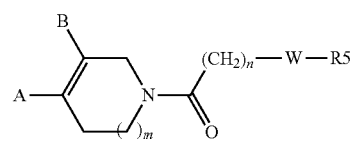

in which:
m represents 0 or 1;
A represents:

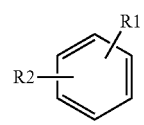

and B represents a hydrogen atom
or
A represents a hydrogen atom and B represents:

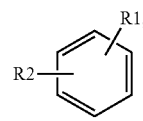

W— is a nitrogenous heterocycle chosen from:

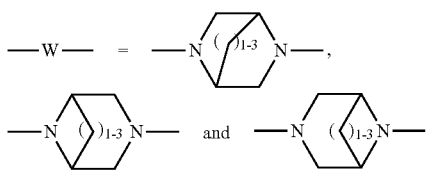

1-3 represents 1, 2 or 3;
n represents 1 or 2;
R1 represents a halogen atom, a $(C_1-C_4)$alkyl group, a trifluoromethyl radical, a $(C_1-C_4)$alkoxy group or a trifluoromethoxy radical;
R2 represents a hydrogen atom, a halogen atom, a $(C_1-C_4)$ alkyl group, a trifluoromethyl radical, a $(C_1-C_4)$alkoxy group, a trifluoromethoxy radical, a COOR group or a $CONH_2$ group;
R5 represents a group of formula:

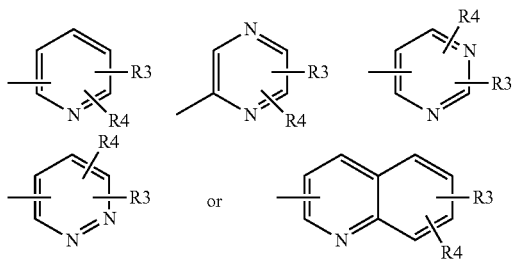

in which R3 and R4, located on any one of the available positions, independently represent a hydrogen atom, a halogen atom, a $(C_1-C_4)$alkyl or $(C_1-C_4)$alkoxy group, a trifluoromethyl or trifluoromethoxy radical, a cyano, or a COOH, COOalkyl, $CONH_2$, CONR6R7 or NHCOR group;
R, R6 and R7 represent a $C_1-C_6$ alkyl group.

The compounds of Formula (I) may contain one or more asymmetrical carbon atoms. They may therefore exist in the form of enantiomers or of diastereoisomers. These enantiomers and diastereoisomers, and also mixtures thereof, including racemic mixtures, are part of the invention.

The compounds of Formula (I) may exist in the form of bases or addition salts with acids. Such addition salts are part of the invention.

These salts may be prepared with pharmaceutically acceptable acids, but the salts of other acids that are useful, for example, for purifying or isolating the compounds of Formula (I) are also part of the invention.

In the context of the present invention:
the term "a halogen atom" is intended to mean: a fluorine, a chlorine, a bromine or an iodine;
the term "an alkyl group" is intended to mean: a linear or branched, saturated aliphatic group. By way of examples, mention may be made of a $C_1-C_4$ alkyl group that may represent a methyl, ethyl, propyl, isopropyl, butyl, isobutyl or tert-butyl;
the term "a fluoroalkyl group" is intended to mean: an alkyl group of which one or more of the hydrogen atoms has (have) been substituted with a fluorine atom;
the term "a perfluoroalkyl group" is intended to mean: an alkyl group of which all the hydrogen atoms have been substituted with a fluorine atom, for example trifluoroalkyl;
the term "an alkoxy group" is intended to mean: an —O-alkyl radical where the alkyl group is as defined above.

Among the compounds of Formula (I) which are subjects of the invention, another group of compounds is constituted of the compounds of Formula (I) in which:
m represents 0 or 1;
A represents:

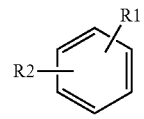

and B represents a hydrogen atom
or
A represents a hydrogen atom and B represents:

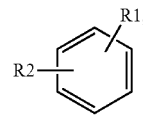

W is a group of formula:

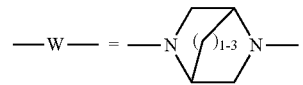

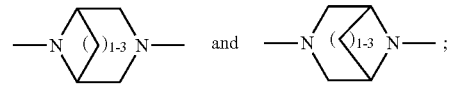

or else

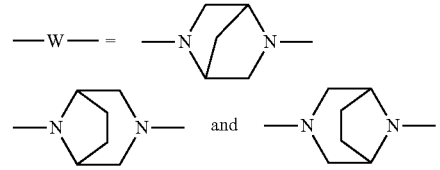

n=1 or 2; or else n=1;
R1 is a halogen atom or a trifluoromethyl radical;
R2 is a hydrogen atom, a trifluoromethyl radical, a COOR group or a $CONH_2$ group;
R5 represents a group of formula:

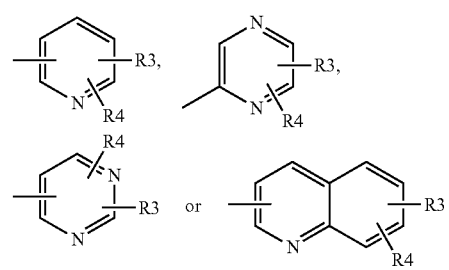

R3 or R4 independently represents a hydrogen atom, a halogen, or a trifluoromethyl, CONH$_2$, COOH or NHCOCH$_3$ radical; or else

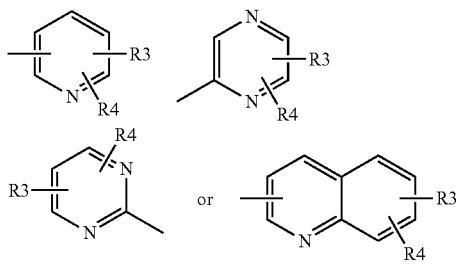

R3 represents a hydrogen atom, a halogen, or a trifluoromethyl, CONH$_2$, COOH or NHCOCH$_3$ radical, and R4 a hydrogen atom; in the form of a base or of an addition salt with an acid.

Among the compounds of Formula (I) which are subjects of the invention, another group of compounds is constituted by the compounds of Formula (I) in which:

m represents 1;
A represents:

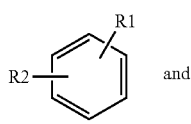

and and B represents a hydrogen atom;
W— is a nitrogenous heterocycle chosen from:

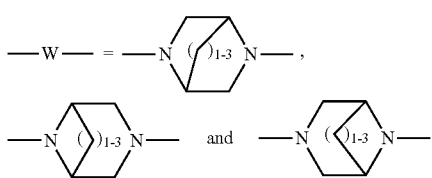

1-3 represents 1, 2 or 3;
n represents 1 or 2;
R1 represents a halogen atom, a (C$_1$-C$_4$)alkyl group, a trifluoromethyl radical, a (C$_1$-C$_4$)alkoxy group or a trifluoromethoxy radical;
R2 represents a hydrogen atom, a halogen atom, a (C$_1$-C$_4$) alkyl group, a trifluoromethyl radical, a (C$_1$-C$_4$)alkoxy group or a trifluoromethoxy radical;
R5 represents a group of formula:

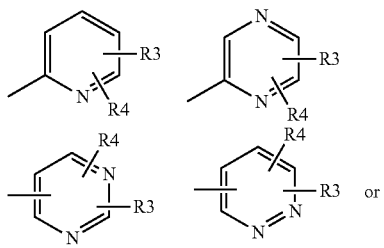

or

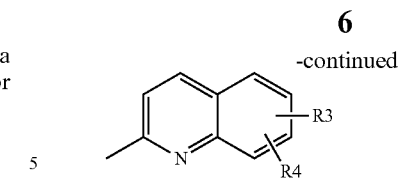

in which R3 and R4, located on any one of the available positions, independently represent a hydrogen atom, a halogen atom, a (C$_1$-C$_4$)alkyl or (C$_1$-C$_4$)alkoxy group, a trifluoromethyl or trifluoromethoxy radical, a cyano, or a COOH or COOalkyl group;

in the form of a base or of an addition salt with an acid.

Among the compounds of Formula (I) which are subjects of the invention, another group of compounds is constituted by the compounds of Formula (I) in which:

m represents 1;
A represents:

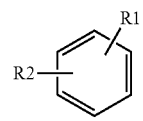

and B represents a hydrogen atom;
W is a group of formula:

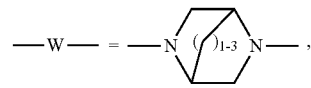

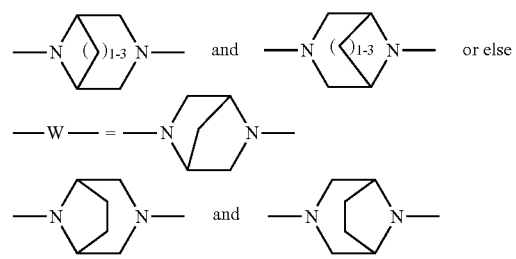

n=1 or 2; or else n=1;
R1 is a halogen atom or a trifluoromethyl radical;
R2 is a hydrogen atom or a trifluoromethyl radical;
R5 represents a group of formula:

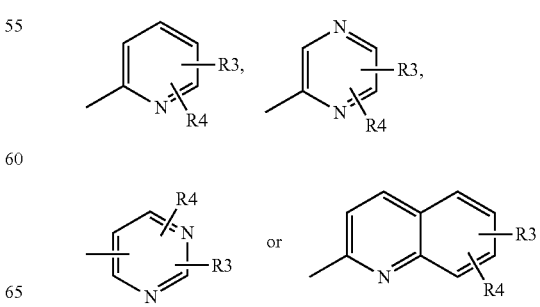

R3 or R4 independently represents a hydrogen atom, a halogen or a trifluoromethyl radical; or else

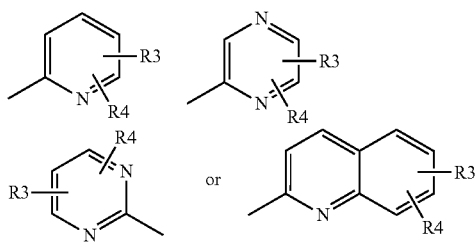

R3 represents a hydrogen atom, a halogen or a trifluoromethyl radical, and R4 a hydrogen atom;
in the form of a base or of an addition salt with an acid.

Among the compounds of Formula (I) which are subjects of the invention, mention may in particular be made of the following compounds:

Compound No. 1: 1-[4-(3-trifluoromethylphenyl)-3,6-dihydro-2H-pyridin-1-yl]-2-[8-(5-trifluoromethylpyridin-2-yl)-3,8-diazabicyclo[3.2.1]oct-3-yl]ethanone;

Compound No. 2: 1-[4-(4-chlorophenyl)-3,6,-dihydro-2H-pyridin-1-yl]-2-(8-pyrimidin-2-yl-3,8-diazabicyclo[3.2.1]oct-3-yl)ethanone;

Compound No. 3: 2-(3-pyrazin-2-yl-3,8-diazabicyclo[3.2.1]oct-8-yl)-1-[4-(3-trifluoromethylphenyl)-3,6-dihyro-2H-pyridin-1-yl]ethanone;

Compound No. 4: 2-(8-pyrimidin-2-yl-3,8-diazabicyclo[3.2.1]oct-3-yl)-1-[4-(3-trifluoromethylphenyl)-3,6-dihydro-2H-pyridin-1-yl]ethanone;

Compound No. 5: 1-[4-(3-trifluoromethylphenyl)-3,6-dihydro-2H-pyridin-1-yl]-2-[3-(5-trifluoromethylpyridin-2-yl)-3,8-diazabicyclo[3.2.1]oct-8-yl]ethanone;

Compound No. 6: 2-(8-pyridin-2-yl-3,8-diazabicyclo[3.2.1]oct-3-yl)-1-[4-(3-trifluoromethylphenyl)-3,6-dihydro-2H-pyridin-1-yl]ethanone;

Compound No. 7: 1-[4-(4-chlorophenyl)-3,6-dihydro-2H-pyridin-1-yl]-2-[8-(5-trifluoromethylpyridin-2-yl)-3,8-diazabicyclo[3.2.1]oct-3-yl]ethanone;

Compound No. 8: 1-[4-(4-chloro-3-trifluoromethylphenyl)-3,6-dihydro-2H-pyridin-1-yl]-2-[8-(5-trifluoromethylpyridin-2-yl)-3,8-diazabicyclo[3.2.1]oct-3-yl]ethanone;

Compound No. 9: 2-(8-quinolin-2-yl-3,8-diazabicyclo[3.2.1]oct-3-yl)-1-[4-(3-trifluoromethylphenyl)-3,6-dihydro-2H-pyridin-1-yl]ethanone;

Compound No. 10: 1-[4-(4-chlorophenyl)-3,6-dihydro-2H-pyridin-1-yl]-2-[3-(5-trifluoromethylpyridin-2-yl)-3,8-diazabicyclo[3.2.1]oct-8-yl]ethanone;

Compound No. 11: 1-[4-(4-chloro-3-trifluoromethylphenyl)-3,6-dihydro-2H-pyridin-1-yl]-2-[8-(5-fluoropyrimidin-2-yl)-3,8-diazabicyclo[3.2.1]oct-3-yl]ethanone;

Compound No. 12: 2-[8-(5-bromopyrimidin-2-yl)-3,8-diazabicyclo[3.2.1]oct-3-yl]-1-[4-(4-chloro-3-trifluoromethylphenyl)-3,6-dihydro-2H-pyridin-1-yl]ethanone;

Compound No. 13: 1-[4-(3-trifluoromethylphenyl)-3,6-dihydro-2H-pyridin-1-yl]-2-[5-(5-trifluoromethylpyridin-2-yl)-2,5-diazabicyclo[2.2.1]hept-2-yl]ethanone;

Compound No. 14: 1-[4-(4-chlorophenyl)-3,6-dihydro-2H-pyridin-1-yl]-2-[5-(5-trifluoromethylpyridin-2-yl)-2,5-diazabicyclo[2.2.1]hept-2-yl]ethanone;

Compound No. 15: 1-[4-(4-chloro-3-trifluoromethylphenyl)-3,6-dihydro-2H-pyridin-1-yl]-2-[5-(5-trifluoromethylpyridin-2-yl)-2,5-diazabicyclo[2.2.1]hept-2-yl]ethanone;

Compound No. 16: 1-[4-(4-chloro-3-trifluoromethylphenyl)-3,6-dihydro-2H-pyridin-1-yl]-2-(5-pyridin-2-yl-2,5-diazabicyclo[2.2.1]hept-2-yl)ethanone;

Compound No. 17: 1-[4-(4-chloro-3-trifluoromethylphenyl)-3,6-dihydro-2H-pyridin-1-yl]-2-[5-(5-fluoropyrimidin-2-yl)-2,5-diazabicyclo[2.2.1]hept-2-yl]ethanone;

Compound No. 18: 1-[4-(4-chloro-3-trifluoromethylphenyl)-3,6-dihydro-2H-pyridin-1-yl]-2-[9-(5-trifluoromethylpyridin-2-yl)-3,9-diazabicyclo[3.3.1]non-3-yl]ethanone;

Compound No. 19: 2-[8-(5-fluoropyrimidin-2-yl)-3,8-diazabicyclo[3.2.1]oct-3-yl]-1-[4-(4-trifluoromethylphenyl)-3,6-dihydro-2H-pyridin-1-yl]ethanone;

Compound No. 20: 1-[4-(3-chlorophenyl)-3,6-dihydro-2H-pyridin-1-yl]-2-[8-(5-fluoropyrimidin-2-yl)-3,8-diazabicyclo[3.2.1]oct-3-yl]ethanone;

Compound No. 21: 2-[8-(5-fluoropyrimidin-2-yl)-3,8-diazabicyclo[3.2.1]oct-3-yl]-1-[4-(3-trifluoromethylphenyl)-3,6-dihydro-2H-pyridin-1-yl]ethanone;

Compound No. 22: 1-[4-(4-chlorophenyl)-3,6-dihydro-2H-pyridin-1-yl]-2-[8-(5-fluoropyrimidin-2-yl)-3,8-diazabicyclo[3.2.1]oct-3-yl]ethanone;

Compound No. 23: 1-[4-(3,5-bistrifluoromethylphenyl)-3,6-dihydro-2H-pyridin-1-yl]-2-[8-(5-fluoropyrimidin-2-yl)-3,8-diazabicyclo[3.2.1]oct-3-yl]ethanone;

Compound No. 24: 2-[8-(5-fluoropyrimidin-2-yl)-3,8-diazabicyclo[3.2.1]oct-3-yl]-1-(4-m-tolyl-3,6-dihydro-2H-pyridin-1-yl)ethanone;

Compound No. 25: 1-[4-(4-chloro-3-trifluoromethylphenyl)-3,6-dihydro-2H-pyridin-1-yl]-2-[8-(pyrimidin-2-yl)-3,8-diazabicyclo[3.2.1]oct-3-yl]ethanone;

Compound No. 26: 1-[4-(4-chloro-3-trifluoromethylphenyl)-3,6-dihydro-2H-pyridin-1-yl]-2-[3-(5-fluoropyrimidin-2-yl)-3,8-diazabicyclo[3.2.1]oct-8-yl]ethanone;

Compound No. 27: 1-[4-(4-chloro-3-trifluoromethylphenyl)-3,6-dihydro-2H-pyridin-1-yl]-2-(8-pyridin-3-yl-3,8-diazabicyclo[3.2.1]oct-3-yl)ethanone;

Compound No. 28: 6-(3-{2-[4-(4-chloro-3-trifluoromethylphenyl)-3,6-dihydro-2H-pyridin-1-yl]-2-oxoethyl}-3,8-diazabicyclo[3.2.1]oct-8-yl)nicotinic acid methyl ester;

Compound No. 29: 6-(3-{2-[4-(4-chloro-3-trifluoromethylphenyl)-3,6-dihydro-2H-pyridin-1-yl]-2-oxoethyl}-3,8-diazabicyclo[3.2.1]oct-8-yl)nicotinic acid;

Compound No. 30: 1-[4-(4-chloro-3-trifluoromethylphenyl)-3,6-dihydro-2H-pyridin-1-yl]-2-[8-(6-trifluoromethylpyridin-3-yl)-3,8-diazabicyclo[3.2.1]-oct-3-yl]ethanone;

Compound No. 31: 2-[8-(5-chloropyridin-2-yl)-3,8-diazabicyclo[3.2.1]oct-3-yl]-1-[4-(4-chloro-3-trifluoromethylphenyl)-3,6-dihydro-2H-pyridin-1-yl]ethanone;

Compound No. 32: 1-[4-(4-chloro-3-trifluoromethylphenyl)-3,6-dihydro-2H-pyridin-1-yl]-2-(8-quinolin-2-yl-3,8-diazabicyclo[3.2.1]oct-3-yl)ethanone;

Compound No. 33: 1-[4-(4-chloro-3-trifluoromethylphenyl)-3,6-dihydro-2H-pyridin-1-yl]-2-[8-(5-fluoropyridin-2-yl)-3,8-diazabicyclo[3.2.1]oct-3-yl]ethanone;

Compound No. 34: 2-[8-(6-chloropyridin-3-yl)-3,8-diazabicyclo[3.2.1]oct-3-yl]-1-[4-(4-chloro-3-trifluoromethylphenyl)-3,6-dihydro-2H-pyridin-1-yl]ethanone;

Compound No. 35: 1-[4-(3-trifluoromethylphenyl)-3,6-dihydro-2H-pyridin-1-yl]-2-[8-(3-trifluoromethylpyridin-2-yl)-3,8-diazabicyclo[3.2.1]oct-3-yl]ethanone;

Compound No. 36: 6-(3-{2-[4-(4-chloro-3-trifluoromethylphenyl)-3,6-dihydro-2H-pyridin-1-yl]-2-oxoethyl}-3,8-diazabicyclo[3.2.1]oct-8-yl)nicotinic acid ethyl ester;
Compound No. 37: 2-(8-pyrazin-2-yl-3,8-diazabicyclo[3.2.1]oct-3-yl)-1-[4-(3-trifluoromethylphenyl)-3,6-dihydro-2H-pyridin-1-yl]ethanone;
Compound No. 38: 2-(8-pyrimidin-4-yl-3,8-diazabicyclo[3.2.1]oct-3-yl)-1-[4-(3-trifluoromethylphenyl)-3,6-dihydro-2H-pyridin-1-yl]ethanone;
Compound No. 39: 1-[4-(4-chloro-3-trifluoromethylphenyl)-3,6-dihydro-2H-pyridin-1-yl]-2-(8-pyrazin-2-yl-3,8-diazabicyclo[3.2.1]oct-3-yl)ethanone;
Compound No. 40: 2-(8-pyrazin-2-yl-3,8-diazabicyclo[3.2.1]oct-3-yl)-1-(4-m-tolyl-3,6-dihydro-2H-pyridin-1-yl)ethanone;
Compound No. 41: 2-(3-{2-[4-(4-chloro-3-trifluoromethylphenyl)-3,6-dihydro-2H-pyridin-1-yl]-2-oxoethyl}-3,8-diazabicyclo[3.2.1]oct-8-yl)pyrimidine-5-carboxylic acid methyl ester;
Compound No. 42: 2-(3-{2-[4-(4-chloro-3-trifluoromethylphenyl)-3,6-dihydro-2H-pyridin-1-yl]-2-oxoethyl}-3,8-diazabicyclo[3.2.1]oct-8-yl)pyrimidine-5-carboxylic acid;
Compound No. 43: 1-[4-(4-chloro-3-trifluoromethylphenyl)-3,6-dihydro-2H-pyridin-1-yl]-3-[4-(5-fluoropyrimidin-2-yl)-3,8-diazabicyclo[3.2.1]oct-3-yl]propan-1-one;
Compound No. 44: 1-[4-(4-chloro-3-trifluoromethylphenyl)-3,6-dihydro-2H-pyridin-1-yl]-2-[5-(5-fluoropyrimidin-2-yl)-2,5-diazabicyclo[2.2.2]oct-2-yl]ethanone;
Compound No. 45: 2-[8-(5-fluoropyrimidin-2-yl)-3,8-diazabicyclo[3.2.1]oct-3-yl]-1-[4-(3-methoxyphenyl)-3,6-dihydro-2H-pyridin-1-yl]ethanone;
Compound No. 46: 1-[4-(4-chloro-3-trifluoromethylphenyl)-3,6-dihydro-2H-pyridin-1-yl]-2-[5-(6-trifluoromethylpyridazin-3-yl)-2,5-diazabicyclo[2.2.1]hept-2-yl]ethanone;
Compound No. 47: 2-[8-(5-fluoropyrimidin-2-yl)-3,8-diazabicyclo[3.2.1]oct-3-yl]-1-[3-(3-trifluoromethyl-4-chlorophenyl)-2,5-dihydropyrrol-1-yl]ethanone;
Compound No. 48: 6-(3-{2-[4-(4-chloro-3-trifluoromethylphenyl)-3,6-dihydro-2H-pyridin-1-yl]-2-oxoethyl}-3,8-diazabicyclo[3.2.1]oct-8-yl)nicotinamide;
Compound No. 49: 2-[8-(5-fluoropyrimidin-2-yl)-3,8-diazabicyclo[3.2.1]oct-3-yl]-1-[4-(2,3-dichlorophenyl)-3,6-dihydro-2H-pyridin-1-yl]ethanone;
Compound No. 50: 1-[4-(4-chloro-3-trifluoromethylphenyl)-3,6-dihydro-2H-pyridin-1-yl]-2-[8-(6-fluoropyridin-3-yl)-3,8-diazabicyclo[3.2.1]oct-3-yl]ethanone;
Compound No. 51: 2-[8-(5-fluoropyrimidin-2-yl)-3,8-diazabicyclo[3.2.1]oct-3-yl]-1-[5-(3-trifluoromethylphenyl)-3,6-dihydro-2H-pyridin-1-yl]ethanone;
Compound No. 52: 2-[8-(5-fluoropyrimidin-2-yl)-3,8-diazabicyclo[3.2.1]oct-3-yl]-1-[3-(3-trifluoromethylphenyl)-2,5-dihydropyrrol-1-yl]ethanone;
Compound No. 53: 3-(1-{2-[8-(5-fluoropyrimidin-2-yl)-3,8-diazabicyclo[3.2.1]oct-3-yl]acetyl}-1,2,5,6-tetrahydropyridin-3-yl)benzoic acid methyl ester;
Compound No. 54: 2-[8-(5-fluoropyrimidin-2-yl)-3,8-diazabicyclo[3.2.1]oct-3-yl]-1-[5-(2-trifluoromethylphenyl)-3,6-dihydro-2H-pyridin-1-yl]ethanone;
Compound No. 55: 1-[4-(4-chloro-3-trifluoromethylphenyl)-3,6-dihydro-2H-pyridin-1-yl]-2-(8-pyrimidin-5-yl-3,8-diazabicyclo[3.2.1]oct-3-yl)ethanone;
Compound No. 56: 2-[8-(5-fluoropyrimidin-2-yl)-3,8-diazabicyclo[3.2.1]oct-3-yl]-1-[4-(3-trifluoromethoxylphenyl)-3,6-dihydro-2H-pyridin-1-yl]ethanone;
Compound No. 57: 1-[4-(4-chloro-3-trifluoromethylphenyl)-3,6-dihydro-2H-pyridin-1-yl]-2-[5-(6-trifluoromethylpyridazin-3-yl)-2,5-diazabicyclo[2.2.2]oct-2-yl]ethanone;
Compound No. 58: N-[6-(3-{2-[4-(4-chloro-3-trifluoromethylphenyl)-3,6-dihydro-2H-pyridin-1-yl]-2-oxoethyl}-3,8-diazabicyclo[3.2.1]oct-8-yl)pyridin-3-yl]acetamide;
Compound No. 59: 2-(8-quinolin-3-yl-3,8-diazabicyclo[3.2.1]oct-3-yl)-1-[4-(3-trifluoromethyl-4-chlorophenyl)-3,6-dihydro-2H-pyridin-1-yl]ethanone;
in the form of a base or of an addition salt with an acid.

In the subsequent text, the term "protective group Pg" is intended to mean a group which makes it possible, on the one hand, to protect a reactive function such as a hydroxyl or an amine during a synthesis, and, on the other hand, to regenerate the intact reactive function at the end of the synthesis. Examples of protective groups and of the methods of protection and of deprotection are given in *Protective Groups in Organic Synthesis*, Green et al., 2nd edition (John Wiley & Sons, Inc., New York).

In accordance with the invention, the compounds of general Formula (I) can be prepared according to the process which follows.

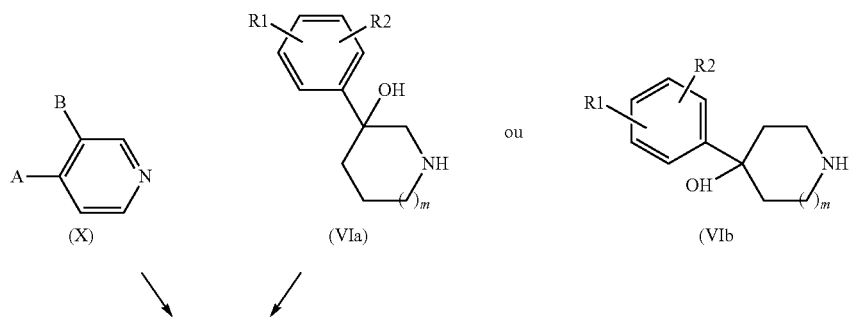

-continued

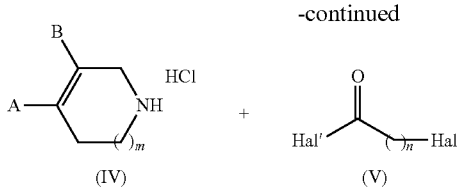

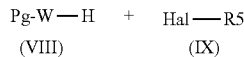

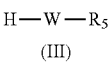

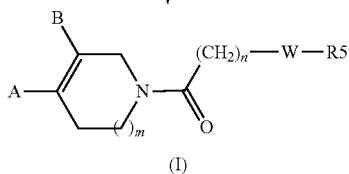

More specifically, the process for preparing the compounds of general Formula (I), in which A, B, m, n, W and R5 are as defined above, comprises reacting a compound of Formula (II):

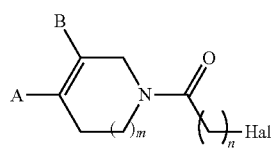

in which A, B, m and n are defined as in general Formula (I) and Hal represents a halogen atom, for example chlorine, and a compound of general Formula (III):

H—W—R5          (III)

in which W and R5 are defined as in general Formula (I), according to methods known to those skilled in the art, for example in the presence of a base, in a solvent as described in WO 03/104225. Thus, by way of a base, mention may be made of organic bases such as triethylamine, N,N-diisopropylamine, diisopropylethylamine (DPEA) or N-methylmorpholine, or alkali metal carbonates or bicarbonates, such as potassium carbonate, sodium carbonate or sodium bicarbonate, and in the absence or presence of an alkali metal iodide, such as potassium iodide or sodium iodide. The reaction is carried out in a solvent such as acetonitrile, N,N-dimethylformamide (DMF), N-methylpyrrolidinone, toluene or propan-2-ol, and at a temperature of between ambient temperature and the reflux temperature of the solvent. The term "ambient temperature" is intended to mean a temperature between 5 and 25° C. By way of example, the reaction may be carried out in the presence of sodium bicarbonate and sodium iodide in a solvent such as DMF.

In the products of general Formula (I) thus obtained, R, R1, R2, R3, R4, R6 and R7 may be modified by treatments commonly used by those skilled in the art, for instance by hydrolysis of an ester group so as to give a carboxylic group.

Generally, the acid addition salts of the compounds of general Formula (I) can be obtained by addition of the appropriate acid, such as hydrochloric acid, hydrobromic acid or oxalic acid.

The compounds of Formula (III), optionally in the form of salts, can be prepared from the corresponding compounds of Formula (VII):

Pg-W—R5          (VII)

in which W and R5 are as defined in Formula (I) and Pg represents a protective group for a nitrogen atom of W. Preferably, Pg is a benzyl group and the deprotection is carried out according to conventional methods well known to those skilled in the art, for example by catalytic hydrogenation on Pd/C or by treatment with chloroformates and then hydrolysis in an acidic medium.

The compounds of Formula (VII) can be prepared from the compounds of Formula (VIII):

Pg-W—H          (VIII)

and (IX):

Hal-R5          (IX)

in which Pg, W and R5 are defined as above and Hal' represents a halogen atom, preferably chlorine. This reaction is generally carried out under the same conditions as the reaction for preparing the compounds of Formula (I) from the compounds of Formulae (II) and (III).

Alternatively, the compounds of Formula (III) can be prepared by the Buchwald coupling method in the presence of an opportunely chosen palladium catalyst and an opportunely chosen phosphine, using inert solvents such as toluene or xylene as solvent, at a temperature between ambient temperature and 110° C.

Examples of such reactions are described in the experimental section.

The compounds of Formula (II) can be obtained by reacting a corresponding compound of Formula (IV):

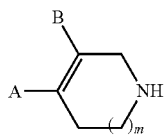
(IV)

in which A, B and m are defined as in general Formula (I), optionally in the form of an acid addition salt;
and a compound of Formula (V):

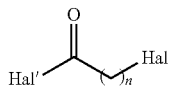
(V)

in which Hal and n are as defined in Formula (II) and Hal' represents a halogen atom, which may be identical to or different from Hal. Preferably, Hal' represents a chlorine atom.

This reaction is generally carried out in the presence of a base, such as triethylamine, N,N-diisopropylethylamine or N-methylmorpholine, in a solvent such as dichloromethane, chloroform, tetrahydrofuran, dioxane or a mixture of these solvents, and at a temperature between 0° C. and ambient temperature. The compounds of Formula (V) are generally commercially available.

The compounds of Formula (IV), optionally in the form of an acid addition salt, can be obtained from the compounds of Formula (VI) (a) or (b):

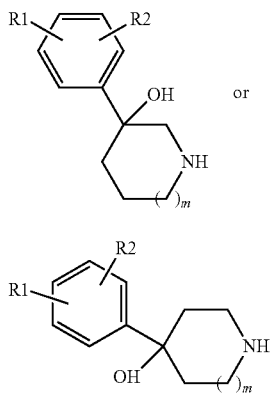

in which R1, R2 and m are as defined above, by dehydration.

The dehydration is carried out in an acidic medium, using, for example, concentrated hydrochloric acid or an acetic acid/hydrochloric acid mixture or an acetic acid/sulphuric acid mixture, at a temperature between ambient temperature and 140° C. The reaction can also be carried out using p-toluene-sulphonic acid in a solvent such as toluene and at a temperature between ambient temperature and the reflux temperature.

Alternatively, the compounds of Formula (IV), when m is =1, can be prepared from a compound of Formula (X)

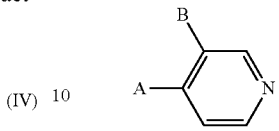

in which A and B are as defined above, by formation of the quaternary benzylammonium salt, followed by reduction with sodium borohydride in solvents such as methanol or dioxane, at a temperature between 0° C. and ambient temperature, and by a debenzylation reaction carried out according to conventional methods, known to those skilled in the art, for example by catalytic hydrogenation on Pd/C or by treatment with chloroformates and then hydrolysis in an acidic medium.

Examples of such reactions are described in the experimental section.

Optionally, the process according to the invention comprises the subsequent step consisting in isolating the desired product obtained.

The products of formulae (VI), (V), (VIII), (IX) and (X) and the reactants, when the method for preparing them is not described, are commercially available or described in the literature, or else can be prepared according to methods which are described or known to those skilled in the art.

According to another of its aspects, a subject of the invention is also compounds of Formula (II)

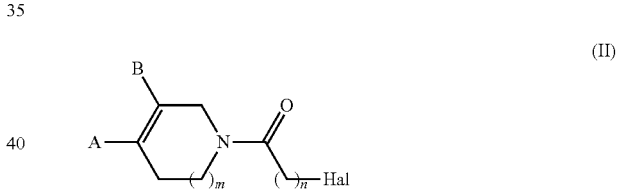
(II)

in which A, B, m, n and Hal are defined as above; in the form of a base or an addition salt with an acid. These compounds are useful as synthesis intermediates for the compounds of Formula (I).

The following examples describe the preparation of some compounds in accordance with the invention. These examples are not limiting and merely illustrate the present invention. The numbers of the compounds exemplified refer back to those given in the table hereinafter, which illustrates the chemical structures and the physical properties of some compounds according to the invention.

The physicochemical measurements were carried out in the following way:

The melting points were measured with a Buchi B540 machine.

The proton nuclear magnetic resonance ($^1$H NMR) spectra were recorded under the following conditions:
a) at 500 MHz on a Bruker machine equipped with an Avance III console;
b) at 400 MHz on a Bruker machine equipped with an Avance I console.

The chemical shifts are reported in ppm relative to the TMS frequency.

All the spectra were recorded at the temperature of 40° C.

The abbreviations used to characterize the signals are the following:
s=singlet, bs=broad singlet, m=multiplet, bm=broad multiplet, d=doublet, bd=broad doublet, t=triplet, q=quadruplet.
*=non-integrable owing to interference with a broad peak due to water.
**=non-integrable owing to interference with a peak due to the NMR solvent.
2Xm=two partially superimposed multiplets.
The HPLC was carried out by means of a ThermoElectron LCQ Deca XP Max system equipped with an ion-trap mass spectrometry detector and a diode array detector.
The conditions for analysis by liquid chromatography coupled to mass spectrometry (LC/UV/MS) are the following:
Chromatographic system A
Eluent A=$H_2O$+0.01% TFA
Eluent B=$CH_3CN$
Gradient of 98% of A to 95% of B in 10 minutes, then elution with 95% of B for 5 minutes.
Flow rate 0.5 ml/minute; temperature 40° C.
Injection of 2 µl of solution at 0.1 mg/ml in a mixture of $CH_3CN:H_2O$=9:1
Chromatographic system B
Eluent A=$H_2O$+0.05% TFA
Eluent B=$CH_3CN$+0.035% TFA
Gradient of 98% of A to 95% of B in 12 minutes, then elution with 95% of B for 3 minutes.
Flow rate 0.7 ml/minute; temperature 40° C.
Injection of 2 µl of solution at 0.1 mg/ml in a mixture of $CH_3CN:H_2O$=9:1
Chromatographic system C
Eluent A=5 mM ammonium acetate buffer, pH 6.5
Eluent B=$CH_3CN$
Gradient of 98% of A to 95% of B in 10 minutes, then elution with 95% of B for 5 minutes.
Flow rate 0.5 ml/minute; temperature 40° C.
Injection of 2 µl of solution at 0.1 mg/ml in a mixture of $CH_3CN:H_2O$=9:1
Chromatographic system D
Eluent A=$H_2O$+0.005% TFA
Eluent B=$CH_3CN$'
Gradient of 95% of A to 90% of B in 17 minutes, then elution with 90% of B for 5 minutes.
Flow rate 0.3 ml/minute; temperature 30° C.
Injection of 2 µl of solution at 0.1 mg/ml in a mixture of $CH_3CN:H_2O$=9:1
Chromatographic system E
Eluent A=5 mM ammonium acetate buffer, pH 6.5
Eluent B=$CH_3CN$
Gradient of 95% of A to 90% of B in 17 minutes, then elution with 90% of B for 5 minutes.
Flow rate 0.3 ml/minute; temperature 30° C.
Injection of 2 µl of solution at 0.1 mg/ml in a mixture of $CH_3CN:H_2O$=9:1
Chromatographic system F
Eluent A=$H_2O$+0.005% TFA
Eluent B=$CH_3CN$
Gradient of 95% of A to 90% of B in 22 minutes, then elution with 90% of B for 7 minutes.
Flow rate 0.3 ml/minute; temperature 40° C. Injection of 2 µl of solution at 0.1 mg/ml in a mixture of $CH_3CN:H_2O$=9:1
Chromatographic system G
Eluent A=$H_2O$+0.01% TFA
Eluent B=$CH_3CN$
Gradient of 80% of A to 60% of B in 15 minutes, then of 60% of A to 100% of B in 5 minutes, then elution with 100% of B for 5 minutes.
Flow rate 0.4 ml/minute; temperature 40° C. Injection of 2 µl of solution at 0.1 mg/ml in a mixture of $CH_3CN:H_2O$=9:1
Chromatographic system H
Eluent A=$H_2O$+0.01% TFA
Eluent B=$CH_3CN$
Gradient of 80% of A to 95% of B in 19 minutes, then elution with 95% of B for 3 minutes.
Flow rate 0.5 ml/minute; temperature 40° C.
Injection of 2 µl of solution at 0.1 mg/ml in a mixture of $CH_3CN:H_2O$=9:1
The products are detected by UV at 220 nm.
The columns used are C18 columns with a particle size between 2 and 4 µm, preferably of 3.5 µm.
For the mass spectrometry part:
Ionisation mode: positive electrospray (ESI+)
Sweeping from 100 to 1200 uma.
The thin layer chromatography was carried out on Merck silica gel 60 TLC plates. The silica gel for the flash column chromatography is sold by Biotage.
All the solvents used are of "reagent grade" or "HPLC grade" purity.

Preparation 1

2-[8-(5-trifluoromethylpyridin-2-yl)-3,8-diazabicyclo[3.2.1]octane hydrochloride 0.9 g of 2-chloro-5-(trifluoromethyl)pyridine (IX), 1 g of 1-benzyl-3,8-diazabicyclo[3.2.1]octane, 0.75 g of potassium carbonate and 0.33 g of NaI are charged to 8 ml of DMF. The reaction is carried out in a Biotage® microwave initiator for 30 min at 160° C. The resulting product is then poured into a saturated aqueous solution of sodium chloride and the mixture is extracted with ethyl acetate. The organic phase is dried over $Na_2SO_4$, filtered, and evaporated under vacuum. 1.5 g of an oily material are isolated and are purified by flash chromatography on a Biotage® column, the eluent being 98/2 cyclohexane/ethyl acetate. 440 mg of a light oil are isolated. 0.44 g of the compound obtained in the preceding stage in 20 ml of ethanol, 2 ml of isopropanol. HCl, in the presence of 0.14 g of 10% Pd/C, is hydrogenated at 45° C. under atmospheric pressure for 4 hours. The resulting product is filtered and evaporated under vacuum and 350 mg of the title product are isolated in the form of a white solid.

Preparation 2

2-[8-(5-fluoropyrimidin-2-yl)-3,8-diazabicyclo[3.2.1]octane hydrochloride 1.44 g of 2-chloro-5-fluoropyrimidine, 2.2 g of 1-benzyl-3,8-diazabicyclo[3.2.1]octane, 1.7 g of potassium carbonate and 0.73 g of NaI are charged to 27 ml of N-methylpyrrolidone. The mixture is heated at 110° C. for 5 hours. It is then poured into a saturated aqueous solution of sodium chloride and the resulting mixture is extracted with ethyl acetate. The organic phase is dried over $Na_2SO_4$, filtered and evaporated under vacuum. 3.2 g of an oily material are isolated and are purified by flash chromatography on a Biotage® column, the eluent being 95/5 cyclohexane/ethyl acetate. 1.4 g of a white solid are isolated and dissolved in 35 ml of 1,2-dichloroethane. 0.72 ml of 1-chloroethylchloroformate is added at 0° C. and the mixture is left to stir under a stream of nitrogen for 10 minutes at 0° C. and then for 3 hours at 85° C. The solvent is evaporated off and 35 ml of methanol are added. The resulting mixture is heated for 30 minutes at the reflux temperature. The solvent is evaporated off and the residue is treated with isopropanol. A white solid is obtained and filtered off, and 900 mg of the title product are isolated. M.p. 236-239° C.

Preparation 3

2-[8-(3-pyridin-2-yl)-3,8-diazabicyclo[3.2.1]octane hydrochloride 0.39 g of 3-bromopyridine, 1 g of 1-benzyl-3,8-diazabicyclo[3.2.1]octane, 0.07 g of palladium acetate, 0.34 g of sodium tert-butoxide and 0.06 g of tri-tert-butylphosphine are charged to 8 ml of o-xylene. The mixture is heated at 120° C. for 6 hours. The resulting product is filtered through celite and the solvent is evaporated off. 1.3 g of an oily material are isolated and are purified by flash chromatography on a Biotage® column, the eluent being 6/4 cyclohexane/ethyl acetate. 700 mg of a light oil are isolated. The product of the preceding stage, in 29 ml of ethanol, 2 ml of isopropanol. HCl, in the presence of 0.35 g of 10% Pd/C, is hydrogenated at 40° C. under atmospheric pressure for 4 hours. The resulting product is filtered and evaporated under vacuum and 500 mg of the title product are isolated in the form of a white solid.

Preparation 4

3,8-diazabicyclo[3.2.1]oct-8-ylnicotinic acid methyl ester hydrochloride 0.42 g of methyl 6-chloronicotinate (IX), 0.5 g of 1-benzyl-3,8-diazabicyclo[3.2.1]octane, 0.4 g of potassium carbonate and 0.17 g of NaI are charged to 7 ml of N-methylpyrrolidone. The mixture is heated for 7 hours at 110° C. It is then poured into a saturated aqueous solution of sodium chloride and the resulting mixture is extracted with ethyl acetate. The organic phase is dried over Na$_2$SO$_4$, filtered and evaporated under vacuum. 1.1 g of an oily material are isolated and are purified by flash chromatography on a Biotage® column, the eluent being 8/2 cyclohexane/ethyl acetate. 520 mg of a light oil are isolated. The product obtained in the preceding stage, in 20 ml of ethanol, 2 ml of isopropanol. HCl, in the presence of 0.22 g of 10% Pd/C, is hydrogenated at 40° C. under atmospheric pressure for 2 hours. The resulting product is filtered and evaporated under vacuum, and 440 mg of the title product are isolated in the form of a white solid.

Preparation 5

4-(3-trifluoromethylphenyl)-1,2,3,6-tetrahydropyridine hydrochloride

In a round-bottomed flask equipped with a mechanical stirrer, 50 g of 4-(3-trifluoromethylphenyl)-4-piperidinol are charged to 377 ml of water and 514 ml of concentrated hydrochloric acid. The mixture is left to react at reflux for 5 hours and is then cooled to ambient temperature. A white solid precipitates. It is filtered off through a Büchner funnel and dried in an oven. 37 g of a white solid are isolated. M.p. 203-204° C.

Preparation 6

4-(3-trifluoromethyl-4-chlorophenyl)-1,2,3,6-tetrahydropyridine hydrochloride

By carrying out the process as described in preparation 5, but using 4-(3-trifluoromethyl-4-chlorophenyl)-4-piperidinol in place of 4-(3-trifluoromethylphenyl)-4-piperidinol, the title compound is obtained. M.p. 263-265° C.

Preparation 7

3-(1,2,5,6-tetrahydropyridin-3-yl)benzoic acid methyl ester hydrochloride 10.9 g of 3-(pyridin-3-yl)benzoic acid methyl ester, 90 ml of toluene and 8.72 g of benzyl bromide are charged, and the mixture is heated at the reflux temperature for 8 hours. The resulting product is evaporated and treated with diisopropyl ether. 19.65 g of a solid are obtained and dissolved in 540 ml of methanol. 3.7 g of sodium borohydride are added slowly at 0° C. and the mixture is stirred at ambient temperature for 30 minutes.

The solvent is evaporated off, the residue is taken up with water and the resulting product is extracted with ethyl acetate. The organic phase is dried over Na$_2$SO$_4$, filtered and evaporated under vacuum. 18 g of an oily material are isolated and are purified by flash chromatography, the eluent being 8/2 cyclohexane/ethyl acetate. 10 g of an oil are isolated. The product of the preceding stage, in 200 ml of methanol, 5 ml of isopropanol. HCl, in the presence of 1.2 g of 10% Pd/C, is hydrogenated at 40° C. under atmospheric pressure for 2 hours. The resulting product is filtered and evaporated under vacuum, and 440 mg of the title product are isolated in the form of a white solid. M.p. 160-162° C.

Preparation 8

2-chloro-1-[4-(3-trifluoromethylphenyl)-3,6-dihydro-2H-pyridin-1-yl]ethanone

In a round-bottomed flask equipped with a mechanical stirrer, 3.44 g of the compound of preparation 5 are suspended in 33.5 ml of dichloromethane. 3.8 ml of triethylamine are added and the mixture is brought to 0° C. At 0° C., 1.01 ml of chloroacetyl chloride, i.e. the compound of general Formula (V) in which Hal=Hal'=Cl and n=1, are run in dropwise. The mixture is left to react for 1 and a half hours and is poured into water. The resulting mixture is extracted with dichloromethane. The organic phase is dried over Na$_2$SO$_4$, filtered and evaporated under vacuum. 4.1 g of a dark oily fat are isolated, triturated, and then left to stand in the cold. The resulting product is separated by settling out and the supernatant is evaporated off under vacuum. 420 mg of a light oil are isolated.

Preparation 9

2-chloro-1-[4-(3-trifluoromethyl-4-chlorophenyl)-3,6-dihydro-2H-pyridin-1-yl]ethanone By carrying out the process as described in preparation 8, but using the compound of preparation 6 in place of the compound of preparation 5 and by purifying the crude product by flash chromatography, the title compound is obtained in the form of a white solid.

Preparation 10

2-(chloroacetyl)-1,2,5,6-tetrahydropyridin-3-ylbenzoic acid methyl ester

By carrying out the process as described in preparation 9, but using the compound of preparation 7 in place of the compound of preparation 6, the title compound is obtained in the form of a white solid.

EXAMPLE 1

Compound No. 1: 1-[4-(3-trifluoromethylphenyl)-3,6-dihydro-2H-pyridin-1-yl]-2-[8-(5-trifluoromethylpyridin-2-yl)-3,8-diazabicyclo[3.2.1]oct-3-yl]ethanone and the oxalate thereof 0.19 g of the compound obtained in preparation 1, 0.18 g of the compound obtained in preparation 8, 0.18 g of potassium carbonate and 0.04 g of NaI are reacted in 4.5 ml of DMF. The reaction is carried out by means of a Biotage® microwave initiator for 30 min at 180° C. The resulting product is poured into water and the resulting mixture is extracted with ethyl acetate. The organic phase is dried over $Na_2SO_4$, filtered and evaporated under vacuum. 250 mg of an oily material are isolated. It is purified on a column by flash chromatography using a Biotage® column, elution being carried out with an 8/2 mixture of cyclohexane/ethyl acetate. 100 mg of oil are isolated. 80 mg of a white solid are obtained by salification with oxalic acid.

NMR (Machine b). δ (ppm, dmso-d6): 1.80-2.05 (m, 4H), 2.41-2.6 (m, **), 2.59-2.84 (m, 3H), 3.5 (bs, 1H), 3.31 (bs, 1H), 3.69 (m, 1H), 3.76 (m, 1H), 4.12 (s, 1H), 4.33 (s, 1H), 4.66 (bs, 2H), 6.36 (m, 1H), 6.87 (m, 1H), 7.57-7.67 (m, 2H), 7.70-7.82 (m, 3H), 8.40 (bs, 1H).

EXAMPLE 2

Compound No. 11: 1-[4-(3-trifluoromethyl-4-chlorophenyl)-3,6-dihydro-2H-pyridin-1-yl]-2-[8-(5-fluoropyrimidin-2-yl)-3,8-diazabicyclo[3.2.1]oct-3-yl]ethanone 40.1 g of the compound obtained in preparation 9, 26.6 g of the compound obtained in preparation 2, 30 ml of diisopropylethylamine and 1500 ml of DMF are reacted together. The mixture is heated for 3 hours at 100° C. The resulting product is poured into water and the resulting mixture is extracted with ethyl acetate. The organic phase is dried over $Na_2SO_4$, filtered and evaporated under vacuum. 69 g of an oily material are isolated. It is purified on a column by flash chromatography using a column that is eluted with a 7/3 mixture of hexane/ethyl acetate. 42.14 g of the title product are isolated. Said product is treated with diethyl ether, the resulting product is filtered, and 33.45 g of a white solid are obtained.

NMR (Machine a). δ (ppm, dmso-d6): 1.72-1.98 (m, 4H), 2.38 (m, 2H), 2.45-2.54 (m, **), 2.56-2.74 (m, 3H), 3.14 (s, 1H), 3.18 (s, 1H), 3.68 (m, 1H), 3.78 (m, 1H), 4.12 (bs, 1H), 4.36 (bs, 1H), 4.59 (m, 2H), 6.38+6.41 (2Xm, 1H), 7.70 (d, J=8.5 Hz, 1H), 7.75 (bd, J=8.5 Hz, 1H), 7.82 (bd, J=2 Hz, 1H), 8.42 (bs, 2H).

EXAMPLE 3

Compound No. 27: 1-[4-(3-trifluoromethyl-4-chlorophenyl)-3,6-dihydro-2H-pyridin-1-yl]-2-[8-(−3-pyridin-2-yl)-3,8-diazabicyclo[3.2.1]oct-3-yl]ethanone By carrying out the process as described in Example 2, but using the compound of preparation 3 in place of the compound of preparation 2, the title compound is obtained in the form of a free base.

NMR (Machine a). δ (ppm, dmso-d6): 1.77-1.98 (m, 4H), 2.40-2.67 (m, **), 3.09 (s, 1H), 3.13 (s, 1H), 3.68 (m, 1H), 3.77 (m, 1H), 4.11 (bs, 1H), 4.26-4.40 (m, 3H), 6.38 (m, 0.5H), 6.42 (m, 0.5H), 7.11-7.22 (m, 2H), 7.71 (d, J=8.5 Hz, 1H), 7.76 (bd, J=8.5 Hz, 1H), 7.82 (bd, J=2 Hz, 1H), 7.86 (bs, 1H), 8.19 (m, 1H).

EXAMPLE 4

Compound No. 28: 6-(3-{2-[4-(4-chloro-3-trifluoromethylphenyl)-3,6-dihydro-2H-pyridin-1-yl]-2-oxoethyl}-3,8-diazabicyclo[3.2.1]oct-8-yl)nicotinic acid methyl ester and the hydrochloride thereof By carrying out the process as described in Example 2, but using the compound of preparation 4 in place of the compound of preparation 2, the title compound is obtained in the form of a free base. It is dissolved in diethyl ether and a solution of isopropanol saturated with HCl is added, and the formation of the hydrochloride in the form of a vitreous solid is obtained.

NMR (Machine a). δ (ppm, dmso-d6): 2.12 (m, 2H), 2.24 (m, 2H), 2.46-2.55 (m, **), 2.60 (bs, 1H), 3.27 (m, 2H), 3.46-3.64 (m, 3H), 3.72 (m, 1H), 3.83 (s, 3H), 4.05 (bs, 1H), 4.17 (bs, *), 4.20-4.36 (m, *), 4.89 (bs, 2H), 6.37 (m, 1H), 6.97 (d, J=9.0 Hz, 1H), 7.69-7.78 (m, 2H), 7.80 (m, 1H), 8.07 (m, 1H), 8.71 (m, 1H), 9.4-10.1 (bs, 1H).

EXAMPLE 5

Compound No. 29: 6-(3-{2-[4-(4-chloro-3-trifluoromethylphenyl)-3,6-dihydro-2H-pyridin-1-yl]-2-oxoethyl}-3,8-diazabicyclo[3.2.1]oct-8-yl)nicotinic acid and the fumarate thereof 0.35 g of the compound of Example 4 is dissolved in 3 ml of an aqueous solution of HCl at 35%. The resulting solution is heated at the reflux temperature for one hour, and washed with ethyl ether. The pH is adjusted to 5 with a solution of NaOH and extraction is carried out with ethyl acetate. After drying and evaporation of the organic phase, 220 mg of a vitreous solid are obtained. Said solid is dissolved in isopropanol and a solution of fumaric acid in isopropanol is added. The fumarate precipitates and is filtered off.

70 mg of title product are isolated in the form of a white solid.

NMR (Machine a). δ (ppm, dmso-d6): 1.74-2.07 (m, 4H), 2.31-2.55 (m, **), 2.58-2.76 (m, 3H), 3.09-3.36 (m, *), 3.68 (m, 1H), 3.78 (m, 1H), 4.12 (bs, 1H), 4.35 (bs, 1H), 4.64 (bs, 2H), 6.40 (m, 1H), 6.64 (s, 2H), 6.76 (m, 1H), 7.71 (d, J=8.5 Hz, 1H), 7.76 (m, 1H), 7.82 (bs, 1H), 7.91 (m, 1H), 8.62 (bs, 1H), 12.1-13.4 (m, 2H).

EXAMPLE 6

Compound No. 53: 3-(1-{2-[8-(5-fluoropyrimidin-2-yl)-3,8-diazabicyclo[3.2.1]oct-3-yl]acetyl}-1,2,5,6-tetrahydropyridin-3-yl)benzoic acid methyl ester By carrying out the process as described in Example 2, but using the compound of preparation 10 in place of the compound of preparation 9, the title compound is obtained in the form of a free base.

NMR (Machine a). δ (ppm, dmso-d6): 1.66 (m, 2H), 1.78-1.99 (m, 2H), 2.23-2.35 (m, 2H), 2.35-2.46 (m, 2H), 2.57-2.75 (m, 2H), 3.19 (s, 2H), 3.61 (m, 1H), 3.70 (m, 1H), 3.88 (s, 3H), 4.34 (s, 1H), 4.50-4.72 (m, 3H), 6.41 (m, 0.5H), 6.46 (m, 0.5H), 7.54 (m, 1H), 7.76 (m, 1H), 7.89 (m, 1H), 7.96 (bs, 0.5H), 8.02 (bs, 0.5H), 8.43 (m, 2H).

The following table describes the examples obtained by application and/or adaptation of described methods using the appropriate reactants and starting products:

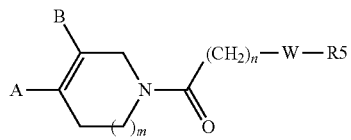

| N | A | B | m | W | R5 | n | Sel | PF | LCMS |
|---|---|---|---|---|---|---|---|---|---|
| 1 | 3-CF₃-phenyl | H | 1 | 2,5-diazabicyclo[2.2.1] | 6-methyl-3-CF₃-pyridin-2-yl | 1 | Oxalate | 217–219 | MH+ 525 r.t. 14.9 Method F |
| 2 | 4-Cl-phenyl | H | 1 | 2,5-diazabicyclo[2.2.1] | 2-methylpyrimidin-2-yl | 1 | — | 181–183 | MH+ 424 r.t. 8.6 Method A |
| 3 | 3-CF₃-phenyl | H | 1 | 2,5-diazabicyclo[2.2.1] | 2-methylpyrazin-2-yl | 1 | Oxalate | — | M+ = 458 r.t. 10.9 Method E |
| 4 | 3-CF₃-phenyl | H | 1 | 2,5-diazabicyclo[2.2.1] | 2-methylpyrimidin-2-yl | 1 | HCl | — | M+ = 458 r.t. 8.8 Method D |
| 5 | 3-CF₃-phenyl | H | 1 | 2,5-diazabicyclo[2.2.1] | 6-methyl-3-CF₃-pyridin-2-yl | 1 | Oxalate | — | M+ = 525 r.t. 11.8 Method F |
| 6 | 3-CF₃-phenyl | H | 1 | 2,5-diazabicyclo[2.2.1] | 6-methylpyridin-2-yl | 1 | Oxalate | 123–126 | MH+ 457 r.t. 8 Method C |
| 7 | 4-Cl-phenyl | H | 1 | 2,5-diazabicyclo[2.2.1] | 6-methyl-3-CF₃-pyridin-2-yl | 1 | Oxalate | 163–164 | MH+ 491 r.t. 9.0 Method C |
| 8 | 4-Cl-3-CF₃-phenyl | H | 1 | 2,5-diazabicyclo[2.2.1] | 6-methyl-3-CF₃-pyridin-2-yl | 1 | Oxalate | 214–215 | MH+ 559 r.t. 7.2 Method A |
| 9 | 3-CF₃-phenyl | H | 1 | 2,5-diazabicyclo[2.2.1] | 2-methylquinolin-2-yl | 1 | — | — | M+ = 507 r.t. 6.1 Method A |
| 10 | 4-Cl-phenyl | H | 1 | 2,5-diazabicyclo[2.2.1] | 6-methyl-3-CF₃-pyridin-2-yl | 1 | Oxalate | — | M+ = 491 r.t. 5.7 Method A |
| 11 | 4-Cl-3-CF₃-phenyl | H | 1 | 2,5-diazabicyclo[2.2.1] | 2-methyl-5-F-pyrimidin-2-yl | 1 | — | 128–130 | |

-continued

| N | A | B | m | W | R5 | n | Sel | PF | LCMS |
|---|---|---|---|---|---|---|---|---|---|
| 12 | 4-Cl, 3-CF$_3$-phenyl | H | 1 | 2,5-diazabicyclo | 5-Br-2-methylpyrimidin-... | 1 | — | 147-149 | MH+ 570 r.t. 6.8 Method A |
| 13 | 3-CF$_3$-phenyl | H | 1 | 2,5-diazabicyclo | 5-CF$_3$-2-methylpyridin-... | 1 | Oxalate | — | M+ = 511 r.t. 13.0 Method C |
| 14 | 4-Cl-phenyl | H | 1 | 2,5-diazabicyclo | 5-CF$_3$-2-methylpyridin-... | 1 | Oxalate | 129-131 | MH+ 477 r.t. 8.0 Method G |
| 15 | 4-Cl, 3-CF$_3$-phenyl | H | 1 | 2,5-diazabicyclo | 5-CF$_3$-2-methylpyridin-... | 1 | Oxalate | — | M+ = 545 r.t. 6.2 Method A |
| 16 | 4-Cl, 3-CF$_3$-phenyl | H | 1 | 2,5-diazabicyclo | 2-methylpyridin- | 1 | Oxalate | 135-137 | MH+ 477 r.t. 8.1 Method C |
| 17 | 4-Cl, 3-CF$_3$-phenyl | H | 1 | 2,5-diazabicyclo | 5-F-2-methylpyrimidin-... | 1 | HCl | 247-250 | MH+ 496 r.t. 4.7 Method H |
| 18 | 4-Cl, 3-CF$_3$-phenyl | H | 1 | 2,5-diazabicyclo (alt) | 5-CF$_3$-2-methylpyridin-... | 1 | Oxalate | — | M+ = 573 r.t. 7.2 Method A |
| 19 | 4-CF$_3$-phenyl | H | 1 | 2,5-diazabicyclo | 5-F-2-methylpyrimidin-... | 1 | — | 154-155 | MH+ 476 r.t. 6.0 Method A |
| 20 | 3-Cl-phenyl | H | 1 | 2,5-diazabicyclo | 5-F-2-methylpyrimidin-... | 1 | — | 146-147 | MH+ 442 r.t. 5.7 Method A |
| 21 | 3-CF$_3$-phenyl | H | 1 | 2,5-diazabicyclo | 5-F-2-methylpyrimidin-... | 1 | HCl | 227-229 | MH+ 476 r.t. 5.9 Method A |
| 22 | 4-Cl-phenyl | H | 1 | 2,5-diazabicyclo | 5-F-2-methylpyrimidin-... | 1 | — | 157-159 | MH+ 442 r.t. 6.0 Method A |

-continued
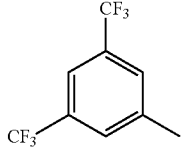
| N | A | B | m | W | R5 | n | Sel | PF | LCMS |
|---|---|---|---|---|---|---|---|---|---|
| 23 |  | H | 1 | 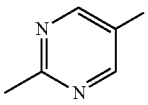 | 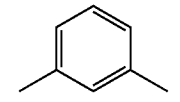 | 1 | HCl | 205-206 | MH+ 544 r.t. 6.9 Method A |
| 24 | 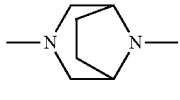 | H | 1 | 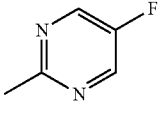 | 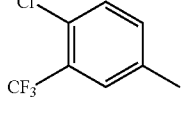 | 1 | — | 133-134 | MH+ 422 r.t. 5.8 Method A |
| 25 | 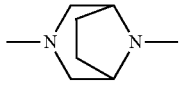 | H | 1 | 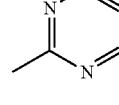 | 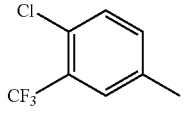 | 1 | — | 120-122 | MH+ 492 r.t. 6.1 Method A |
| 26 | 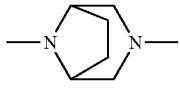 | H | 1 | 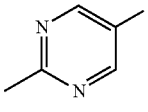 | 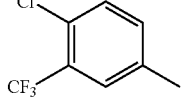 | 1 | HCl | 223-224 | MH+ 510 r.t. 5.6 Method A |
| 27 | 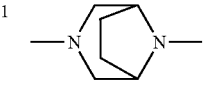 | H | 1 | 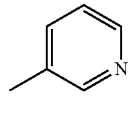 | 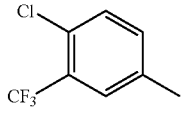 | 1 | — | 136-137 | MH+ 491 r.t. 4.9 Method A |
| 28 |  | H | 1 | 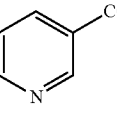 | 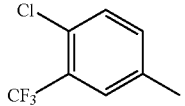 | 1 | HCl | — | M+ = 549 r.t. 6.6 Method A |
| 29 |  | H | 1 | 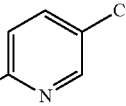 | 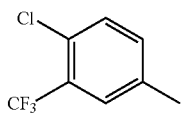 | 1 | fumarate | 165-168 | MH+ 535 r.t. 5.9 Method A |
| 30 |  | H | 1 | 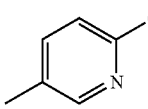 | 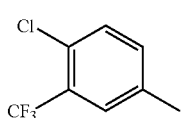 | 1 | — | 161-163 | MH+ 559 r.t. 6.7 Method A |
| 31 | 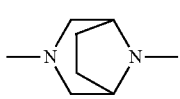 | H | 1 | 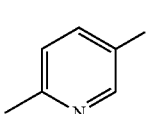 | 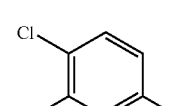 | 1 | oxalate | 219-220 | MH+ 525 r.t. 6.5 Method A |
| 32 | 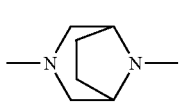 | H | 1 | 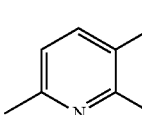 | 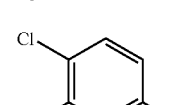 | 1 | oxalate | 135-136 | MH+ 541 r.t. 6.1 Method A |
| 33 | 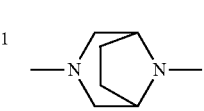 | H | 1 | 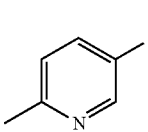 | | 1 | oxalate | 203-204 | MH+ 509 r.t. 6.2 Method A |

-continued

| N | A | B | m | W | R5 | n | Sel | PF | LCMS |
|---|---|---|---|---|---|---|---|---|---|
| 34 | 4-Cl, 3-CF₃-phenyl | H | 1 | 2,5-diazabicyclo[2.2.1] | 6-chloro-pyridin-3-yl (5-methyl) | 1 | oxalate | 212-213 | MH+ 525 r.t. 6.3 Method A |
| 35 | 3-CF₃-phenyl | H | 1 | 2,5-diazabicyclo[2.2.1] | 3-(trifluoromethyl)-2-methyl-pyridin-? | 1 | oxalate | 190-191 | MH+ 525 r.t. 6.0 Method A |
| 36 | 4-Cl, 3-CF₃-phenyl | H | 1 | 2,5-diazabicyclo[2.2.1] | 5-COOEt-6-methyl-pyridin-3-yl | 1 | oxalate | 210-211 | MH+ 563 r.t. 6.9 Method B |
| 37 | 3-CF₃-phenyl | H | 1 | 2,5-diazabicyclo[2.2.1] | 6-methyl-pyrazin-2-yl | 1 | oxalate | 220-221 | MH+ 457 r.t. 5.6 Method B |
| 38 | 3-CF₃-phenyl | H | 1 | 2,5-diazabicyclo[2.2.1] | 4-methyl-pyrimidin-? | 1 | fumarate | 161-163 | MH+ 458 r.t. 5.1 Method A |
| 39 | 4-Cl, 3-CF₃-phenyl | H | 1 | 2,5-diazabicyclo[2.2.1] | 6-methyl-pyrazin-2-yl | 1 | oxalate | 150-151 | MH+ 492 r.t. 5.6 Method A |
| 40 | 3-methyl-phenyl | H | 1 | 2,5-diazabicyclo[2.2.1] | 6-methyl-pyrazin-2-yl | 1 | oxalate | 162-163 | MH+ 404 r.t. 4.4 Method A |
| 41 | 4-Cl, 3-CF₃-phenyl | H | 1 | 2,5-diazabicyclo[2.2.1] | 5-COOCH₃-2-methyl-pyrimidin-? | 1 | — | 152-153 | MH+ 550 r.t. Method A |
| 42 | 4-Cl, 3-CF₃-phenyl | H | 1 | 2,5-diazabicyclo[2.2.1] | 5-COOH-2-methyl-pyrimidin-? | 1 | — | 192-194 | MH+ 536 r.t. 5.5 Method C |
| 43 | 4-Cl, 3-CF₃-phenyl | H | 1 | 2,5-diazabicyclo[2.2.1] | 5-F-2-methyl-pyrimidin-? | 2 | oxalate | 140-141 | MH+ 525 r.t. 5.8 Method A |
| 44 | 4-Cl, 3-CF₃-phenyl | H | 1 | 2,5-diazabicyclo[2.2.1] | 5-F-2-methyl-pyrimidin-? | 1 | — | — | M+ = 510 r.t. 6.1 Method A |

-continued

| N | A | B | m | W | R5 | n | Sel | PF | LCMS |
|---|---|---|---|---|---|---|---|---|---|
| 45 | 3-MeO-phenyl | H | 1 | diazabicyclo | 5-F-2-Me-pyrimidin-yl | 1 | oxalate | 171-172 | MH+ 438 r.t. 5.4 Method B |
| 46 | 4-Cl-3-CF₃-phenyl | H | 1 | diazabicyclo | 3-CF₃-6-Me-pyridazin-yl | 1 | fumarate | 205-207 | MH+ 546 r.t. 6.1 Method B |
| 47 | 4-Cl-3-CF₃-phenyl | H | 0 | diazabicyclo | 5-F-2-Me-pyrimidin-yl | 1 | — | 200-201 | MH+ 496 r.t. 5.6 Method A |
| 48 | 4-Cl-3-CF₃-phenyl | H | 1 | diazabicyclo | 5-CONH₂-6-Me-pyridin-yl | 1 | — | 241-242 | MH+ 534 r.t. 5.0 Method B |
| 49 | 2,3-diCl-phenyl | H | 1 | diazabicyclo | 5-F-2-Me-pyrimidin-yl | 1 | — | 127 | MH+ 476 r.t. 5.7 Method |
| 50 | 4-Cl-3-CF₃-phenyl | H | 1 | diazabicyclo | 6-F-3-Me-pyridin-yl | 1 | oxalate | 160-161 | MH+ 509 r.t. 6.0 Method A |
| 51 | H | 3-CF₃-phenyl | 1 | diazabicyclo | 5-F-2-Me-pyrimidin-yl | 1 | — | 156-157 | MH+ 476 r.t. 5.9 Method A |
| 52 | 3-CF₃-phenyl | H | 0 | diazabicyclo | 5-F-2-Me-pyrimidin-yl | 1 | — | 195-196 | MH+ 462 r.t. 5.5 Method A |
| 53 | H | 3-MeOOC-phenyl | 1 | diazabicyclo | 5-F-2-Me-pyrimidin-yl | 1 | — | 140-143 | MH+ 466 r.t. 5.1 Method A |
| 54 | H | 2-CF₃-phenyl | 1 | diazabicyclo | 5-F-2-Me-pyrimidin-yl | 1 | oxalate | 215-217 | MH+ 476 r.t. 5.6 Method A |
| 55 | 4-Cl-3-CF₃-phenyl | H | 1 | diazabicyclo | 5-Me-pyrimidin-yl | 1 | HCl | 215-217 | MH+ 492 r.t. 5.6 Method A |

-continued

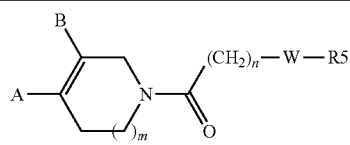

| N | A | B | m | W | R5 | n | Sel | PF | LCMS |
|---|---|---|---|---|---|---|---|---|---|
| 56 | 3-F₃CO-phenyl | H | 1 | diazabicyclooctane | 5-F, 2-methyl-pyrimidine | 1 | — | 135-136 | MH+ 492 r.t. 5.7 Method A |
| 57 | 3-Cl, 4-CF₃-phenyl | H | 1 | diazabicyclooctane | 3-CF₃, 6-methyl-pyridazine | 1 | — | 161-162 | MH+ 560 r.t. 6.4 Method A |
| 58 | 3-Cl, 4-CF₃-phenyl | H | 1 | diazabicyclooctane | 5-NCOCH₃, 2-methyl-pyridine | 1 | — | — | MH+ 549 |
| 59 | 3-Cl, 4-CF₃-phenyl | H | 1 | diazabicyclooctane | 3-methyl-quinoline | 1 | — | — | MH+ 541 r.t. 5.8 Method A |

The compounds according to the invention have been the subject of biochemical studies.

Cell Culture:

The SH-SY-5Y strain (human neuroblastoma) is cultured conventionally in a DMEM culture medium (Dulbecco's Modified Eagle's Medium) (Gibco BRL, France) containing FCS (5%) (foetal calf serum) (Boehringer Mannheim, Germany), sodium pyruvate (1 mM) and glutamine (4 mM) in collagen-coated culture flasks (Becton Dickinson, France).

The parent strain SK-N-BE (human neuroblastoma) and the clone Bep 75, stably expressing the whole form of the human $p75^{NTR}$ receptor (SK-N-BE Bep 75), are cultured conventionally in an RPMI culture medium containing FCS (5%), sodium pyruvate (1 mM) and glutamine (4 mM). For the SK-N-BE Bep 75 cells, hygromycin (200 μl/20 ml of medium) is added as selection agent.

Study of the binding of $^{125}I$ NGF to the $p75^{NTR}$ receptor

The study of NGF binding (nerve growth factor radiolabelled with iodine-125, Amersham-2000 Ci/mmol) is carried out on a cell suspension of the SK-N-BE Bep 75 strain in accordance with the method described by Weskamp (Neuron, 1991, 6, 649-663). The non-specific binding is determined by measuring the total binding after preincubation for one hour with cells at 37° C. in the presence of non-radiolabelled NGF (1 μM). The specific binding is calculated by the difference between the total binding measurement and the non-specific binding measurement. The competition experiments are carried out using an iodinated NGF ($^{125}I$ NGF) concentration of 0.3 nM. The concentrations inhibiting 50% ($IC_{50}$) of the binding of $^{125}I$ NGF to the $p75^{NTR}$ receptor, of the compounds according to the invention, are low and range from $10^{-6}$ to $10^{-11}M$.

The compounds of Formula (I) exhibit an activity in this test, with $IC_{50}$ values which range from $10^{-6}$ to $10^{-11}M$. For example, compounds No. 1, 2, 7 and 11 showed an $IC_{50}$ of 1.35 nM, 0.18 nM, 0.29 nM and 0.98 nM, respectively.

Study of $p75^{NTR}$ receptor dimerisation independently of its ligand

The study of $p75^{NTR}$ receptor dimerisation is carried out on a cell suspension of the SK-N-BE Bep 75 strain. The cells ($2.5 \times 10^4$ cells/well) are placed in wells (96-well plate) for 24 h, and then preincubated for 1 h at 37° C. in the presence or absence of the compounds according to the invention. Supernatant, derived from culturing HEK293 human cells of renal origin expressing, after transfection for 48 h, and secreting a soluble form of the $p75^{NTR}$ receptor (extracellular part of the receptor) coupled to an alkaline phosphatase, is then added at the final concentration of 10 nM. The quantification of the specific binding of the soluble $p75^{NTR}$ receptor to the receptor present on SK-N-BE Bep 75 cells is determined by measuring the enzymatic alkaline phosphatase activity after incubation of the cells for 1 hour at 37° C. in the presence of the supernatant. After filtration and transfer of the filters into 24-well plates, the alkaline phosphatase activity is determined by adding CDP-Star chemiluminescent substrate (ready-to-use, Roche). The concentrations, of the compounds according to the invention, for inhibiting 50% ($IC_{50}$) of the dimerisation of the $p75^{NTR}$ receptor are low and range from $10^{-6}$ to $10^{-11}M$.

The compounds of Formula (I) exhibit an activity in this test, with $IC_{50}$ values which range from $10^{-6}$ to $10^{-11}M$.

For example, compounds No. 1, 3, 8, 11, 27, 28, 29 and 53 showed, respectively, an $IC_{50}$ of 23.4 nM, 0.05 nM, 0.68 nM, 0.2 nM, 0.23 nM, 9.84 nM, 0.14 nM and 2.08 nM.

Measurement of Apoptosis

The cells (human neuroblastoma strains SH-SY-5Y and SK-N-BE Bep 75) are placed in Petri dishes 35 mm in diameter (Biocoat collagen I ($10^5$ cells/well)) in an appropriate culture medium containing 5% FCS for 24 h. The culture medium is then removed, the cells are rinsed with PBS (Dulbecco's Phosphate buffered saline), and then either fresh medium containing 5% FCS, or medium containing NGF (at the concentration of 10 ng/ml) or beta-amyloid peptide (Aβ1-40) (at the concentration of 10 μM) is added, in the presence or absence of the compounds according to the invention. The degrees of apoptosis are measured 48 hours after the treatments in the case of the SH-SY-5Y strain, and 24 hours after the treatments in the case of the SK-N-BE Bep 75 strain, by quantifying the cytoplasmic histones associated with DNA fragments (cell death detection ELISA, Boehringer Mannheim, Germany). The degrees of apoptosis are expressed as quantity of oligonucleosomes/$10^5$ cells. Each value corresponds to the mean of 9 experimental points distributed over 3 independent experiments.

The compounds of Formula (I) has an NGF-induced apoptosis-inhibiting activity, with $IC_{50}$ values which range from $10^{-6}$ to $10^{-11}$M. For example, compounds No. 1, 3, 8, 11, 27 and 29 showed, respectively, an $IC_{50}$ of 1.33 nM, 0.067 nM, 2.24 nM, 0.21 nM, 0.088 nM and 0.22 nM.

Thus, the binding of the compounds according to the invention to the $p75^{NTR}$ receptor is reflected, on the one hand, at the biochemical level, by the inhibition of the dimerisation of the receptor induced by neurotrophins, or independently of the ligand, and, on the other hand, at the cellular level, by the inhibition of the $p75^{NTR}$-receptor-mediated proapoptotic effect.

Thus, according to one of the subjects of the present invention, the compounds of Formula (I) exhibit a very advantageous inhibitory activity on $p75^{NTR}$ receptor dimerisation independently of its ligand.

The compounds according to the invention can therefore be used for the preparation of medicaments, in particular of medicaments for preventing or treating any pathology in which the $p75^{NTR}$ receptor is involved, more particularly those indicated hereinafter.

The compounds according to the invention can also be used for preventing or treating any pathology in which the $p75^{NTR}$ receptor is involved, more particularly those indicated hereinafter.

Thus, according to another of its aspects, a subject of the invention is medicaments which comprise a compound of Formula (I), or an addition salt of the latter with a pharmaceutically acceptable acid.

Thus, the compounds according to the invention may be used, in humans or in animals, in the treatment or prevention of various $p75^{NTR}$-dependent conditions, such as central and peripheral neurodegenerative diseases, for instance senile dementia, epilepsy, Alzheimer's disease, Parkinson's disease, Huntington's chorea, Down's syndrome, prion diseases, amnesia, schizophrenia, depression, bipolar disorder; amyotrophic lateral sclerosis, multiple sclerosis; cardiovascular conditions, for instance post-ischaemic cardiac damage, cardiomyopathies, myocardial infarction, heart failure, cardiac ischaemia, cerebral infarction; peripheral neuropathies (of diabetic, traumatic or iatrogenic origin); damage to the optic nerve and to the retina (retinal pigment degeneration, glaucoma); retinal ischaemia; macular degeneration; spinal chord traumas and cranial traumas; atherosclerosis; stenoses; healing disorders; alopecia.

The compounds according to the invention can also be used in the treatment of cancers, for instance lung cancer, thyroid cancer, pancreatic cancer, prostate cancer, cancer of the small intestine and of the colon, breast cancer, and in the treatment of tumours, metastases and leukaemias.

The compounds according to the invention can also be used in the treatment of respiratory disorders, for instance pulmonary inflammation, allergy and asthma, or chronic obstructive pulmonary disease.

The compounds according to the invention can also be used in the treatment of cutaneous pain (of the skin, the subcutaneous tissues and the associated organs), somatic pain, visceral pain (at the level of the circulatory, respiratory, gastrointestinal or urogenital system), and neurological pain.

The compounds according to the invention can be used in the treatment of chronic neuropathic and inflammatory pain and in the treatment of autoimmune diseases such as rheumatoid arthritis.

The compounds according to the invention can also be used in the treatment of diseases such as ankylosing spondylarthritis, psoriatic arthritis or plaque psoriasis.

The compounds according to the invention can also be used in the treatment of bone fractures, or in the treatment or prevention of bone diseases such as osteoporosis.

According to another of its aspects, the present invention concerns pharmaceutical compositions comprising, as active ingredient, a compound according to the invention. These pharmaceutical compositions contain an effective dose of at least one compound according to the invention, or a pharmaceutically acceptable salt of said compound, and also at least one pharmaceutically acceptable excipient.

Said excipients are chosen, according to the pharmaceutical form and the method of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of Formula (I) above, or the salt thereof, can be administered in unit administration form, as a mixture with conventional pharmaceutical excipients, to animals and to humans, for the prevention or treatment of the above conditions or diseases.

The appropriate unit administration forms comprise oral administration forms such as tablets, soft or hard gel capsules, powders, granules and oral solutions or suspensions, sublingual, buccal, intratracheal, intraocular or intranasal administration forms, forms for administration by inhalation, topical, parenteral, such as transdermal, subcutaneous, intramuscular or intravenous administration forms, rectal administration forms, and implants. For topical application, the compounds according to the invention can be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

The dose of active ingredient administered per day may reach 0.01 to 100 mg/kg, in one or more intakes, preferably 0.02 to 50 mg/kg. In general, the daily dose of the compound according to the invention will be the lowest effective dose of the compound capable of producing a therapeutic effect.

There may be particular cases where higher or lower dosages are appropriate; such dosages do not depart from the context of the invention. According to the usual practice, the dosage appropriate for each patient is determined by the physician according to the method of administration and the weight and response of said patient.

According to another of its aspects, the present invention also concerns a method for treating the pathologies indicated above, which comprises the administration, to a patient, of an effective dose of a compound according to the invention, or a pharmaceutically acceptable salt thereof.

The invention claimed is:

1. A compound corresponding to Formula (I):

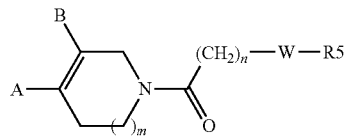

in which:

m represents 0 or 1;

A represents:

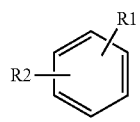

and B represents a hydrogen atom or

A represents a hydrogen atom and B represents:

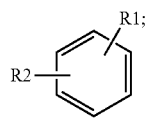

W— is a nitrogenous heterocycle chosen from:

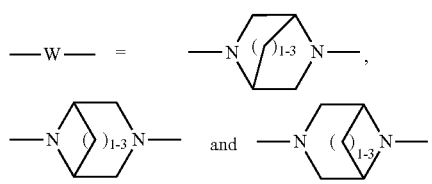

1-3 represents 1, 2 or 3;

n represents 1 or 2;

R1 represents a halogen atom, a $(C_1-C_4)$alkyl group, a trifluoromethyl group, a $(C_1-C_4)$alkoxy group or a trifluoromethoxy group;

R2 represents a hydrogen atom, a halogen atom, a $(C_1-C_4)$ alkyl group, a trifluoromethyl group, a $(C_1-C_4)$alkoxy group, a trifluoromethoxy group, a COOR group or a $CONH_2$ group;

R5 represents a group of formula:

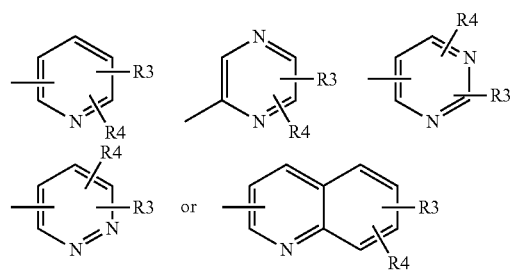

in which R3 and R4, located on any one of the available positions, independently represent a hydrogen atom, a halogen atom, a $(C_1-C_4)$alkyl or $(C_1-C_4)$alkoxy group, a trifluoromethyl or trifluoromethoxy group, a cyano, or a COOH, COOalkyl, $CONH_2$, CONR6R7 or NHCOR group;

R, R6 and R7 represent a $C_1-C_6$ alkyl group;

in the form of a base or of a pharmaceutically acceptable addition salt with an acid.

2. A compound according to claim 1, in which R2 is a hydrogen atom, a trifluoromethyl group, a COOR group or a $CONH_2$ group; in the form of a base or of a pharmaceutically acceptable addition salt with an acid.

3. A compound according to claim 1, in which R5 represents a group of formula:

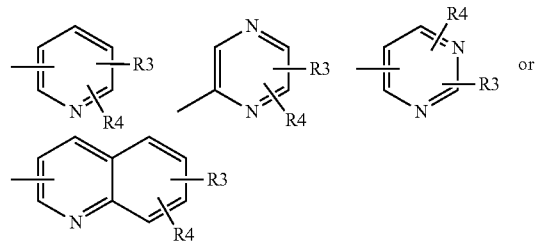

where R3 and R4 independently represent a hydrogen atom, a halogen, or a trifluoromethyl, $CONH_2$, COON or $NHCOCH_3$ group; in the form of a base or of a pharmaceutically acceptable addition salt with an acid.

4. A compound according to claim 1, wherein:

m represents 1;

A represents:

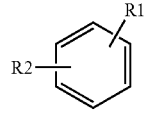

and B represents a hydrogen atom;

W— is a nitrogenous heterocycle chosen from:

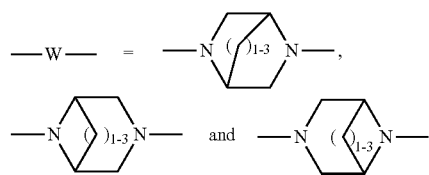

n represents 1 or 2;

R1 represents a halogen atom, a (C$_1$-C$_4$)alkyl group, a trifluoromethyl group, a (C$_1$-C$_4$)alkoxy group or a trifluoromethoxy group;

R2 represents a hydrogen atom, a halogen atom, a (C$_1$-C$_4$) alkyl group, a trifluoromethyl group, a (C$_1$-C$_4$)alkoxy group or a trifluoromethoxy group;

R5 represents a group of formula:

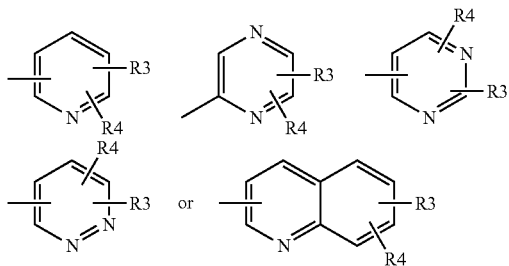

in which R3 and R4, located on any one of the available positions, independently represent a hydrogen atom, a halogen atom, a (C$_1$-C$_4$)alkyl or (C$_1$-C$_4$)alkoxy group, a trifluoromethyl, trifluoromethoxy or cyano group, or a COOH or COOalkyl group; in the form of a base or of a pharmaceutically acceptable addition salt with an acid.

5. A compound according to claim 1, wherein W is a group of formula chosen from:

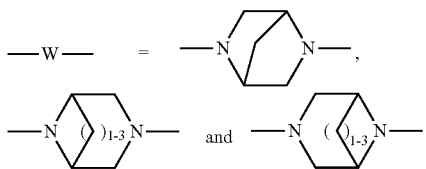

in the form of a base or of a pharmaceutically acceptable addition salt with an acid.

6. A compound according to claim 1, wherein n =1; in the form of a base or of a pharmaceutically acceptable addition salt with an acid.

7. A compound according to claim 1, wherein R1 is a halogen atom or a trifluoromethyl group; in the form of a base or of a pharmaceutically acceptable addition salt with an acid.

8. A compound according to claim 1, wherein R2 is a hydrogen atom or a trifluoromethyl group; in the form of a base or of a pharmaceutically acceptable addition salt with an acid.

9. A compound according to claim 1, wherein R5 represents a group of formula:

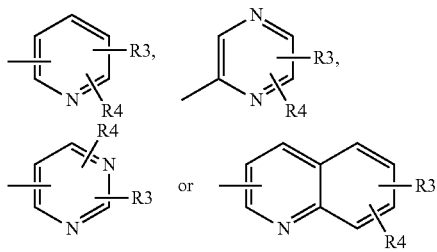

where R3 and R4 independently represent a hydrogen or halogen atom or a trifluoromethyl group; in the form of a base or of a pharmaceutically acceptable addition salt with an acid.

10. A compound according to claim 1, chosen from the following compounds:

Compound No. 1: 1-[4-(3-trifluoromethylphenyl)-3,6-dihydro-2H-pyridin-1-yl]-2-[8-(5-trifluoromethylpyridin-2-yl)-3,8-diazabicyclo[3.2.1]oct-3-yl]ethanone;

Compound No. 2: 1-[4-(4-chlorophenyl)-3,6,-dihydro-2H-pyridin-1-yl]-2-(8-pyrimidin-2-yl-3,8-diazabicyclo[3.2.1]oct-3-yl)ethanone;

Compound No. 3: 2-(3-pyrazin-2-yl-3,8-diazabicyclo[3.2.1]oct-8-yl)-1-[4-(3-trifluoromethylphenyl)-3,6-dihyro-2H-pyridin-1-yl]ethanone;

Compound No. 4: 2-(8-pyrimidin-2-yl-3,8-diazabicyclo[3.2.1]oct-3-yl)-1-[4-(3-trifluoromethylphenyl)-3,6-dihydro-2H-pyridin-1-yl]ethanone;

Compound No. 5: 1-[4-(3-trifluoromethylphenyl)-3,6-dihydro-2H-pyridin-1-yl]-2-[3-(5-trifluoromethylpyridin-2-yl)-3,8-diazabicyclo[3.2.1]oct-8-yl]ethanone;

Compound No. 6: 2-(8-pyridin-2-yl-3,8-diazabicyclo[3.2.1]oct-3-yl)-1-[4-(3-trifluoromethylphenyl)-3,6-dihydro-2H-pyridin-1-yl]ethanone;

Compound No. 7: 1-[4-(4-chlorophenyl)-3,6-dihydro-2H-pyridin-1-yl]-2-[8-(5-trifluoromethylpyridin-2-yl)-3,8-diazabicyclo[3.2.1]oct-3-yl]ethanone;

Compound No. 8: 1-[4-(4-chloro-3-trifluoromethylphenyl)-3,6-dihydro-2H-pyridin-1-yl]-2-[8-(5-trifluoromethylpyridin-2-yl)-3,8-diazabicyclo[3.2.1]oct-3-yl]ethanone;

Compound No. 9: 2-(8-quinolin-2-yl-3,8-diazabicyclo[3.2.1]oct-3-yl)-1-[4-(3-trifluoromethylphenyl)-3,6-dihydro-2H-pyridin-1-yl]ethanone;

Compound No. 10: 1-[4-(4-chlorophenyl)-3,6-dihydro-2H-pyridin-1-yl]-2-[3-(5-trifluoromethylpyridin-2-yl)-3,8-diazabicyclo[3.2.1]oct-8-yl]ethanone;

Compound No. 11: 1-[4-(4-chloro-3-trifluoromethylphenyl)-3,6-dihydro-2H-pyridin-1-yl]-2-[8-(5-fluoropyrimidin-2-yl)-3,8-diazabicyclo[3.2.1]oct-3-yl]ethanone;

Compound No. 12: 2-[8-(5-bromopyrimidin-2-yl)-3,8-diazabicyclo[3.2.1]oct-3-yl]-1-[4-(4-chloro-3-trifluoromethylphenyl)-3,6-dihydro-2H-pyridin-1-yl]ethanone;

Compound No. 13: 1-[4-(3-trifluoromethylphenyl)-3,6-dihydro-2H-pyridin-1-yl]-2-[5-(5-trifluoromethylpyridin-2-yl)-2,5-diazabicyclo[2.2.1]hept-2-yl]ethanone;

Compound No. 14: 1[4-(4-chlorophenyl)-3,6-dihydro-2H-pyridin-1-yl]-2-[5-(5-trifluoromethylpyridin-2-yl)-2,5-diazabicyclo[2.2.1]hept-2-yl]ethanone;

Compound No. 15: 1-[4-(4-chloro-3-trifluoromethylphenyl)-3,6-dihydro-2H-pyridin-1-yl]-2-[5-(5-trifluoromethylpyridin-2-yl)-2,5-diazabicyclo[2.2.1]hept-2-yl]ethanone;

Compound No. 16: 1-[4-(4-chloro-3-trifluoromethylphenyl)-3,6-dihydro-2H-pyridin-1-yl]-2-(5-pyridin-2-yl-2,5-diazabicyclo[2.2.1]hept-2-yl)ethanone;

Compound No. 17: 1[4-(4-chloro-3-trifluoromethylphenyl)-3,6-dihydro-2H-pyridin-1-yl]-2-[5-(5-fluoropyrimidin-2-yl)-2,5-diazabicyclo[2.2.1]hept-2-yl]ethanone;

Compound No. 18: 1-[4-(4-chloro-3-trifluoromethylphenyl)-3,6-dihydro-2H-pyridin-1-yl]-2-[9-(5-trifluoromethylpyridin-2-yl)-3,9-diazabicyclo[3.3.1]non-3-yl]ethanone;

Compound No. 19: 2-[8-(5-fluoropyrimidin-2-yl)-3,8-diazabicyclo[3.2.1]oct-3-yl]-1-[4-(4-trifluoromethylphenyl)-3,6-dihydro-2H-pyridin-1-yl]ethanone;

Compound No. 20: 1-[4-(3-chlorophenyl)-3,6-dihydro-2H-pyridin-1-yl]-2-[8-(5-fluoropyrimidin-2-yl)-3,8-diazabicyclo[3.2.1]oct-3-yl]ethanone;

Compound No. 21: 2-[8-(5-fluoropyrimidin-2-yl)-3,8-diazabicyclo[3.2.1]oct-3-yl]-1-[4-(3-trifluoromethylphenyl)-3,6-dihydro-2H-pyridin-1-yl]ethanone;

Compound No. 22: 1-[4-(4-chlorophenyl)-3,6-dihydro-2H-pyridin-1-yl]-2-[8-(5-fluoropyrimidin-2-yl)-3,8-diazabicyclo[3.2.1]oct-3-yl]ethanone;

Compound No. 23: 1-[4-(3,5-bistrifluoromethylphenyl)-3,6-dihydro-2H-pyridin-1-yl]-2-[8-(5-fluoropyrimidin-2-yl)-3,8-diazabicyclo[3.2.1]oct-3-yl]ethanone;

Compound No. 24: 2-[8-(5-fluoropyrimidin-2-yl)-3,8-diazabicyclo[3.2.1]oct-3-yl]-1-(4-m-tolyl-3,6-dihydro-2H-pyridin-1-yl)ethanone;

Compound No. 25: 1-[4-(4-chloro-3-trifluoromethylphenyl)-3,6-dihydro-2H-pyridin-1-yl]-2-[8-(pyrimidin-2-yl)-3,8-diazabicyclo[3.2.1]oct-3-yl]ethanone;

Compound No. 26: 1-[4-(4-chloro-3-trifluoromethylphenyl)-3,6-dihydro-2H-pyridin-1-yl]-2-[3-(5-fluoropyrimidin-2-yl)-3,8-diazabicyclo[3.2.1]oct-8-yl]ethanone;

Compound No. 27: 1-[4-(4-chloro-3-trifluoromethylphenyl)-3,6-dihydro-2H-pyridin-1-yl]-2-(8-pyridin-3-yl-3,8-diazabicyclo[3.2.1]oct-3-yl)ethanone;

Compound No. 28: 6-(3-{2-[4-(4-chloro-3-trifluoromethylphenyl)-3,6-dihydro-2H-pyridin-1-yl]-2-oxoethyl}-3,8-diazabicyclo[3.2.1]oct-8-yl)nicotinic acid methyl ester;

Compound No. 29: 6-(3-{2-[4-(4-chloro-3-trifluoromethylphenyl)-3,6-dihydro-2H-pyridin-1-yl]-2-oxoethyl}-3,8-diazabicyclo[3.2.1]oct-8-yl)nicotinic acid;

Compound No. 30: 1-[4-(4-chloro-3-trifluoromethylphenyl)-3,6-dihydro-2H-pyridin-1-yl]-2-[8-(6-trifluoromethylpyridin-3-yl)-3,8-diazabicyclo[3.2.1]oct-3-yl]ethanone;

Compound No. 31: 2-[8-(5-chloropyridin-2-yl)-3,8-diazabicyclo[3.2.1]oct-3-yl]-1-[4-(4-chloro-3-trifluoromethylphenyl)-3,6-dihydro-2H-pyridin-1-yl]ethanone;

Compound No. 32: 1-[4-(4-chloro-3-trifluoromethylphenyl)-3,6-dihydro-2H-pyridin-1-yl]-2-(8-quinolin-2-yl-3,8-diazabicyclo[3.2.1]oct-3-yl)ethanone;

Compound No. 33: 1-[4-(4-chloro-3-trifluoromethylphenyl)-3,6-dihydro-2H-pyridin-1-yl]-2-[8-(5-fluoropyridin-2-yl)-3,8-diazabicyclo[3.2.1]oct-3-yl]ethanone;

Compound No. 34: 2-[8-(6-chloropyridin-3-yl)-3,8-diazabicyclo[3.2.1]oct-3-yl]-1-[4-(4-chloro-3-trifluoromethylphenyl)-3,6-dihydro-2H-pyridin-1-yl]ethanone;

Compound No. 35: 1-[4-(3-trifluoromethylphenyl)-3,6-dihydro-2H-pyridin-1-yl]-2-[8-(3-trifluoromethylpyridin-2-yl)-3,8-diazabicyclo[3.2.1]oct-3-yl]ethanone;

Compound No. 36: 6-(3-{2-[4-(4-chloro-3-trifluoromethylphenyl)-3,6-dihydro-2H-pyridin-1-yl]-2-oxoethyl}-3,8-diazabicyclo[3.2.1]oct-8-yl)nicotinic acid ethyl ester;

Compound No. 37: 2-(8-pyrazin-2-yl-3,8-diazabicyclo[3.2.1]oct-3-yl)-1-[4-(3-trifluoromethylphenyl)-3,6-dihydro-2H-pyridin-1-yl]ethanone;

Compound No. 38: 2-(8-pyrimidin-4-yl-3,8-diazabicyclo[3.2.1]oct-3-yl)-1-[4-(3-trifluoromethylphenyl)-3,6-dihydro-2H-pyridin-1-yl]ethanone;

Compound No. 39: 1-[4-(4-chloro-3-trifluoromethylphenyl)-3,6-dihydro-2H-pyridin-1-yl]-2-(8-pyrazin-2-yl-3,8-diazabicyclo[3.2.1]oct-3-yl)ethanone;

Compound No. 40: 2-(8-pyrazin-2-yl-3,8-diazabicyclo[3.2.1]oct-3-yl)-1-(4-m-tolyl-3,6-dihydro-2H-pyridin-1-yl)ethanone;

Compound No. 41: 2-(3-{2-[4-(4-chloro-3-trifluoromethylphenyl)-3,6-dihydro-2H-pyridin-1-yl]-2-oxoethyl}-3,8-diazabicyclo[3.2.1]oct-8-yl)pyrimidine-5-carboxylic acid methyl ester;

Compound No. 42: 2-(3-{2-[4-(4-chloro-3-trifluoromethylphenyl)-3,6-dihydro-2H-pyridin-1-yl]-2-oxoethyl}-3,8-diazabicyclo[3.2.1]oct-8-yl)pyrimidine-5-carboxylic acid;

Compound No. 43: 1-[4-(4-chloro-3-trifluoromethylphenyl)-3,6-dihydro-2H-pyridin-1-yl]-3-[8-(5-fluoropyrimidin-2-yl)-3,8-diazabicyclo[3.2.1]oct-3-yl]propan-1-one;

Compound No. 44: 1-[4-(4-chloro-3-trifluoromethylphenyl)-3,6-dihydro-2H-pyridin-1-yl]-2-[5-(5-fluoropyrimidin-2-yl)-2,5-diazabicyclo[2.2.2]oct-2-yl]ethanone;

Compound No. 45: 2-[8-(5-fluoropyrimidin-2-yl)-3,8-diazabicyclo[3.2.1]oct-3-yl]-1-[4-(3-methoxyphenyl)-3,6-dihydro-2H-pyridin-1-yl]ethanone;

Compound No. 46: 1-[4-(4-chloro-3-trifluoromethylphenyl)-3,6-dihydro-2H-pyridin-1-yl]-2-[5-(6-trifluoromethylpyridazin-3-yl)-2,5-diazabicyclo[2.2.1]hept-2-yl]ethanone;

Compound No. 47: 2-[8-(5-fluoropyrimidin-2-yl)-3,8-diazabicyclo[3.2.1]oct-3-yl]-1-[3-(3-trifluoromethyl-4-chlorophenyl)-2,5-dihydropyrrol-1-yl]ethanone;

Compound No. 48: 6-(3-{2-[4-(4-chloro-3-trifluoromethylphenyl)-3,6-dihydro-2H-pyridin-1-yl]-2-oxoethyl}-3,8-diazabicyclo[3.2.1]oct-8-yl)nicotinamide;

Compound No. 49: 2-[8-(5-fluoropyrimidin-2-yl)-3,8-diazabicyclo[3.2.1]oct-3-yl]-1-[4-(2,3-dichlorophenyl)-3,6-dihydro-2H-pyridin-1-yl]ethanone;

Compound No. 50: 1-[4-(4-chloro-3-trifluoromethylphenyl)-3,6-dihydro-2H-pyridin-1-yl]-2-[8-(6-fluoropyridin-3-yl)-3,8-diazabicyclo[3.2.1]oct-3-yl]ethanone;

Compound No. 51: 2-[8-(5-fluoropyrimidin-2-yl)-3,8-diazabicyclo[3.2.1]oct-3-yl]-1-[5-(3-trifluoromethylphenyl)-3,6-dihydro-2H-pyridin-1-yl]ethanone;

Compound No. 52: 2-[8-(5-fluoropyrimidin-2-yl)-3,8-diazabicyclo[3.2.1]oct-3-yl]-1-[3-(3-trifluoromethylphenyl)-2,5-dihydropyrrol-1-yl]ethanone;

Compound No. 53: 3-(1-{2-[8-(5-fluoropyrimidin-2-yl)-3,8-diazabicyclo[3.2.1]oct-3-yl]acetyl}-1,2,5,6-tetrahydropyridin-3-yl)benzoic acid methyl ester;

Compound No. 54: 2-[8-(5-fluoropyrimidin-2-yl)-3,8-diazabicyclo[3.2.1]oct-3-yl]-1-[5-(2-trifluoromethylphenyl)-3,6-dihydro-2H-pyridin-1-yl]ethanone;

Compound No. 55: 1-[4-(4-chloro-3-trifluoromethylphenyl)-3,6-dihydro-2H-pyridin-1-yl]-2-(8-pyrimidin-5-yl-3,8-diazabicyclo[3.2.1]oct-3-yl)ethanone;

Compound No. 56: 2-[8-(5-fluoropyrimidin-2-yl)-3,8-diazabicyclo[3.2.1]oct-3-yl]-1-[4-(3-trifluoromethoxylphenyl)-3,6-dihydro-2H-pyridin-1-yl]ethanone;

Compound No. 57: 1-[4-(4-chloro-3-trifluoromethylphenyl)-3,6-dihydro-2H-pyridin-1-yl]-2-[5-(6-trifluoromethylpyridazin-3-yl)-2,5-diazabicyclo[2.2.2]oct-2-yl]ethanone;

Compound No. 58: N-[6-(3-{2-[4-(4-chloro-3-trifluoromethylphenyl)-3,6-dihydro-2H-pyridin-1-yl]-2-oxoethyl}-3,8-diazabicyclo[3.2.1]oct-8-yl)pyridin-3-yl]acetamide; or Compound No. 59: 2-(8-quinolin-3-yl-3,8-diazabicyclo[3.2.1]oct-3-yl)-1-[4-(3-trifluoromethyl-4-chlorophenyl)-3,6-dihydro-2H-pyridin-1-yl]ethanone;

in the form of a base or of a pharmaceutically acceptable addition salt with an acid.

11. A process for preparing a compound of Formula (I) according to claim 1, comprising reacting a compound of Formula (II):

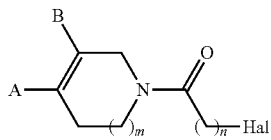
(II)

in which A, B, m and n are as defined in claim 1 and Hal represents a halogen atom, with a compound of general Formula (III):

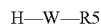
(III)

in which W and R5 are as defined in claim 1.

12. A pharmaceutical composition, comprising a compound of Formula (I) according to claim 1, or a pharmaceutically acceptable salt thereof, and at least one pharmaceutically acceptable excipient.

* * * * *

UNITED STATES PATENT AND TRADEMARK OFFICE
CERTIFICATE OF CORRECTION

PATENT NO. : 8,193,190 B2
APPLICATION NO. : 12/966413
DATED : June 5, 2012
INVENTOR(S) : Marco Baroni et al.

It is certified that error appears in the above-identified patent and that said Letters Patent is hereby corrected as shown below:

On the title page, item (56), in column 2, under "Other Publications", line 31, delete "Humans" and insert -- Human --, therefor.

In column 7, line 27-28, delete "dihyro" and insert -- dihydro --, therefor.

In column 10, line 49, delete "(VIb" and insert -- (VIb) --, therefor.

In column 15, line 43, delete "CH$_3$CN'" and insert -- CH$_3$CN --, therefor.

In column 19, line 58, delete "diazobicyclo" and insert -- diazabicyclo --, therefor.

In column 23-24, line 4, delete "I" and insert -- 1 --, therefor.

In column 23-24, line 5, delete "II" and insert -- 1 --, therefor.

In column 27-28, line 26, delete "r.t." and insert -- r.t. 6.5 --, therefor.

In column 33, line 61, delete "chord" and insert -- cord --, therefor.

In column 36, line 35, in claim 3, delete " 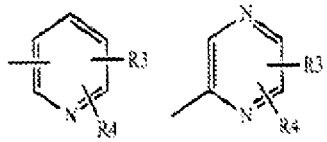 " and insert

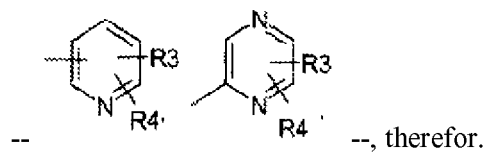 --, therefor.

Signed and Sealed this
Twenty-third Day of October, 2012

David J. Kappos
*Director of the United States Patent and Trademark Office*

CERTIFICATE OF CORRECTION (continued)
U.S. Pat. No. 8,193,190 B2

In column 38, line 6, in claim 10, delete "6,-dihydro" and insert -- 6-dihydro --, therefor.

In column 38, line 11-12, in claim 10, delete "dihyro" and insert -- dihydro --, therefor.

In column 38, line 49, in claim 10, delete "1[4" and insert -- 1-[4 --, therefor.

In column 38, line 60, in claim 10, delete "1[4" and insert -- 1-[4 --, therefor.

In column 39, line 42-43, in claim 10, delete "trifluoromethylphenyl" and insert -- trifluoromethylphenyl --, therefor.

In column 39, line 43, in claim 10, delete "d ihydro" and insert -- dihydro --, therefor.

In column 39, line 52-53, in claim 10, delete "trifluoromethylphenyl" and insert -- trifluoromethylphenyl --, therefor.

In column 39, line 58, in claim 10, delete "pyridin -1-yl" and insert -- pyridin-1-yl --, therefor.